United States Patent
Nakanishi

(10) Patent No.: US 9,216,370 B2
(45) Date of Patent: Dec. 22, 2015

(54) FILM FORMED OF HEMISPHERICAL PARTICLES, METHOD FOR PRODUCING SAME, AND USE OF SAME

(75) Inventor: Takashi Nakanishi, Ibaraki (JP)

(73) Assignee: NATIONAL ISTITUTE FOR MATERIALS SCIENCE, Ibaraki (JP)

(*) Notice: Subject to any disclaimer, the term of this patent is extended or adjusted under 35 U.S.C. 154(b) by 352 days.

(21) Appl. No.: 13/977,981

(22) PCT Filed: Dec. 28, 2011

(86) PCT No.: PCT/JP2011/080404
§ 371 (c)(1),
(2), (4) Date: Aug. 8, 2013

(87) PCT Pub. No.: WO2012/098818
PCT Pub. Date: Jul. 26, 2012

(65) Prior Publication Data
US 2013/0327703 A1 Dec. 12, 2013

(30) Foreign Application Priority Data
Jan. 21, 2011 (JP) ................... 2011-010953

(51) Int. Cl.
*B01D 39/00* (2006.01)
*B01D 39/14* (2006.01)
*B01D 63/00* (2006.01)
(Continued)

(52) U.S. Cl.
CPC .............. *B01D 39/16* (2013.01); *B05D 1/202* (2013.01); *B29C 39/003* (2013.01); *B32B 37/187* (2013.01); *B82Y 30/00* (2013.01); *B82Y 40/00* (2013.01); *C07D 209/58* (2013.01); *Y10T 428/249921* (2015.04); *Y10T 428/268* (2015.01)

(58) Field of Classification Search
CPC ...... B82Y 30/00; B82Y 40/00; B01D 71/024; B01D 69/12; B01D 67/0048; B01D 39/16; B01D 39/003
See application file for complete search history.

(56) References Cited

U.S. PATENT DOCUMENTS

| 8,092,773 B2 * | 1/2012 | Nakanishi ............ C07D 209/70 252/182.1 |
| 2003/0013003 A1 * | 1/2003 | Hinokuma ............. B82Y 30/00 429/521 |

(Continued)

FOREIGN PATENT DOCUMENTS

| JP | 2007-296593 | 11/2007 |
| JP | 2008-115286 | 5/2008 |

(Continued)

OTHER PUBLICATIONS

International Search Report issued Apr. 3, 2012 in International (PCT) Application No. PCT/JP2011/080404.
(Continued)

*Primary Examiner* — Ana Fortuna
(74) *Attorney, Agent, or Firm* — Wenderoth, Lind & Ponack, L.L.P.

(57) ABSTRACT

A film using fullerene derivatives, a method for producing such films, and use of same are provided. In the film formed of hemispherical particles according to the present invention, the hemispherical particles are organized like a hexagonal close-packed structure, and are formed by specific fullerene derivatives. The hemispherical particles preferably have a bilayer membrane structure assembled to provide a flake-like surface for the hemispherical particles.

19 Claims, 25 Drawing Sheets

(51) Int. Cl.

| | |
|---|---|
| *B01D 29/46* | (2006.01) |
| *B01D 39/16* | (2006.01) |
| *B82Y 30/00* | (2011.01) |
| *C07D 209/58* | (2006.01) |
| *B29C 39/00* | (2006.01) |
| *B32B 37/00* | (2006.01) |
| *B05D 1/20* | (2006.01) |
| *B82Y 40/00* | (2011.01) |

(56) References Cited

U.S. PATENT DOCUMENTS

| | | | | |
|---|---|---|---|---|
| 2003/0027870 | A1* | 2/2003 | Wilson | A61K 31/05 514/656 |
| 2006/0073370 | A1* | 4/2006 | Krusic | B82Y 30/00 429/483 |
| 2007/0293693 | A1* | 12/2007 | Krusic | B82Y 30/00 558/425 |
| 2012/0111411 | A1* | 5/2012 | Uetani | B82Y 10/00 136/263 |
| 2012/0119198 | A1* | 5/2012 | Uetani | B82Y 10/00 257/40 |
| 2013/0327703 | A1* | 12/2013 | Nakanishi | B82Y 30/00 210/500.1 |

FOREIGN PATENT DOCUMENTS

| | | |
|---|---|---|
| JP | 2008-303148 | 12/2008 |
| WO | 00/21905 | 4/2000 |

OTHER PUBLICATIONS

Nakanishi et al., "Molecular Self-Organization at Air/Liquid/Liquid Interfaces—Development of Hemispherical Particle-Arrays in Macroscopic Scale-", Polymer Reprints, vol. 60, No. 1, May 10, 2011, p. ROMBUNNO. 3D23, with English abstract.

Chaturbedy et al., "Self-assembly of $C_{60}$, SWNTs and few-layer graphene and their binary composites at the organic-aqueous interface", Journal of Colloid and Interface Science, vol. 360, No. 1, 2011, pp. 249-255.

Nakanishi, Takashi, "Emergent Functions of Multi-shaped Exotic Materials with Fine-tuned Self-orgaizations", CSJ: The Chemical Society of Japan Koen Yokoshu, vol. 91, No. 1, Mar. 11, 2011, p. 144, with English abstract.

Nakanishi et al., "Development of Macroscopic Particle Array Based on Molecular Self-Organization", Japan Society of Applied Physics and Related Societies, vol. 58, Mar. 9, 2011, p. ROMBUNNO. 25A-BG-6.

Nakanishi, Takashi, "Materialization of Supramolecular Assemblies of Fullerenes with Controlled Dimensionality", Shokubai, vol. 52, No. 3, Apr. 10, 2010, pp. 184-189, with English abstract.

Nakanishi, Takashi, "Multi-shaped Supramolecular Materials—Soft Materials and Hard Materials-", Oleoscience, vol. 10, No. 2, Feb. 1, 2010, pp. 63-71, with English abstract.

Nakanishi, Takashi, "Bunshi Kan Sogo Sayo no Seimitsu Seigyo ni yoru Fullerene Sozai Material", Colloid Bukai News Letter, vol. 33, No. 4, 2008, pp. 2-6.

Masuno et al., "Shinki Tanso Sozai—Fullerene Oyobi sono Yudotai Nano-Whisker", Chemistry & Chemical industry, vol. 58, No. 3, Mar. 1, 2005, pp. 265-267.

Bond et al., Electrochemical and Structural Studies on Microcrystals of the $(C_{60})_x(CTV)$ Inclusion Complexes ($_x$=1, 1.5; CTV=cyclotriveratrylene), The Journal of Physical Chemistry, vol. 105, No. 9, pp. 1687-1695.

Meidine et al., "Single Crystal X-Ray Structure of Benzene-solvated $C_{60}$", Journal of the Chemical Society, vol. 20, 1992, pp. 1534-1537.

* cited by examiner

FILM FORMED OF HEMISPHERICAL PARTICLES, METHOD FOR PRODUCING SAME, AND USE OF SAME

TECHNICAL FIELD

The present invention relates to films formed of hemispherical particles, methods for producing such films, and use of same. Specifically, the invention relates to films formed of hemispherical particles that use specific fullerene derivatives, methods for producing such films, and filters using the films.

BACKGROUND ART

Nanocarbons as represented by fullerenes, carbon nanotubes, and carbon nanohorns have attracted interest, and expectations are high for their potential application as electronic material, catalyst, and biological material.

Of particular interest to the present inventor among such nanocarbons is the fullerene derivative, and the present inventor has recently successfully developed a supramolecular assembly assembled from fullerene derivatives (see, for example, Patent Literature 1).

As described in Patent Literature 1, the supramolecular assembly has the nanoassembly backbone constructed from the bilayer membrane structure formed by the fullerene derivatives of the following formula. The fullerene structure based on the bilayer membrane structure is assembled in a lamellar fashion.

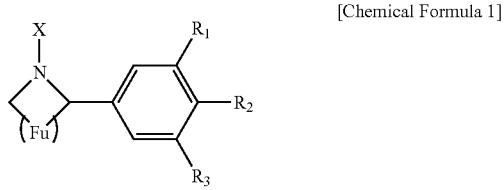

[Chemical Formula 1]

In the formula, $R_1$ and $R_2$ are alkyl chains having at least 20 carbon atoms, and $R_3$ is a hydrogen atom, or an alkyl chain having at least 20 carbon atoms. X is a hydrogen atom or a methyl group. Fu is a fullerene such as $C_{60}$, $C_{70}$ and $C_{76}$.

The supramolecular assembly of Patent Literature 1 has a fractal structure, and exhibits superhydrophobicity. Further, because of the high specific surface area, the supramolecular assembly of Patent Literature 1 can be an adsorption support.

The method for producing the supramolecular assembly of Patent Literature 1 includes the steps of mixing the fullerene derivative of the foregoing formula with 1,4-dioxane, heating the resulting mixture, aging the mixture, and applying a solution that contains the precipitates obtained in the aging step.

However, the supramolecular assembly obtained as above cannot be said as a film of desirable quality, because of the low monodispersity of the fullerene structure. It would thus be desirable if a film of desirable quality could be obtained in which the fullerene derivative bilayer membrane structure provides the nanoassembly backbone.

SUMMARY OF INVENTION

Technical Problem

Under these circumstances, it is an object of the present invention to provide films using fullerene derivatives, methods for producing such films, and use of the films.

Solution to Problem

In the film formed of hemispherical particles according to the present invention, the hemispherical particles are organized like a hexagonal close-packed structure, and are formed by the fullerene derivatives of the formula (1) (wherein X is a hydrogen atom or a methyl group, and (Fu) is any fullerene). The present invention has thus achieved the foregoing object.

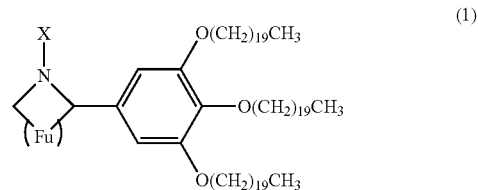

(1)

The hemispherical particles may have a bilayer membrane structure assembled to provide a flake-like surface for the hemispherical particles.

The hemispherical particles may have a particle size ranging from 15 μm to 35 μm.

The fullerene derivatives in the hemispherical particles may be distributed in a manner that makes the fullerene derivative denser at the center of the bottom surface of the hemispherical particles and sparser toward the outer side.

A method for producing the film formed of hemispherical particles according to the present invention includes the following steps. The step of spreading over a water surface a benzene solution dissolving the fullerene derivatives of formula (1) (wherein X is a hydrogen atom or a methyl group, and (Fu) is any fullerene) in benzene.

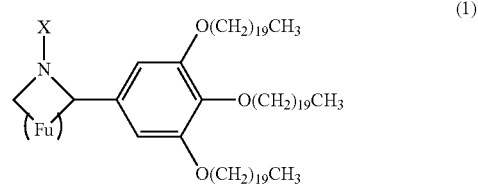

(1)

The step of evaporating the benzene in the benzene solution. The present invention has thus achieved the foregoing object.

The method may further include the step of transferring the film formed of hemispherical particles obtained in the evaporation step to a substrate.

In the spreading step, the benzene solution may be spread in 13.5 μL to 14.5 μL per 1 cm² area of the water surface.

In the spreading step, the benzene solution may have a concentration of from 1.5 mM to 2.5 mM.

In the evaporation step, the benzene solution spread over the water surface may be allowed to stand at room temperature in the dark.

In the evaporation step, the benzene solution spread over the water surface may be allowed to stand under sealed conditions.

The film formed of hemispherical particles may have a bilayer membrane structure formed by the fullerene derivatives, and may be adapted so that the bilayer membrane structure is assembled to provide a flake-like surface for the hemispherical particles, and that the hemispherical particles are arranged like a hexagonal close-packed structure.

The filter of the present invention comprises the film, and the present invention has thus achieved the foregoing object. The film may be adapted to support semiconductor particles.

Advantageous Effects of Invention

In the film of the present invention, the hemispherical particles are arranged like a hexagonal close-packed structure and joined to one another. The film is thus highly orderly and stable. The film of the present invention has a structure reminiscent of the retinal structure of the compound eye of organisms, for example, such as insects. By using the film of the present invention as a template, a material of a novel structure can be provided upon transferring the form of the film of the present invention to material such as metal, polymer and inorganic material.

The film producing method of the present invention includes the steps of spreading over a water surface a benzene solution dissolving a specific fullerene derivative, and evaporating the solvent benzene. Because the benzene is simply evaporated after spreading the benzene solution over a water surface, the method does not require any special and expensive device, can easily provide the film of the present invention at low cost, with an area in excess of 1 $mm^2$. Further, in the method of the present invention, the specific fullerene derivative self-assembles into the hemispherical particles in the foregoing steps, and the hemispherical particles are organized like a hexagonal close-packed structure and can join to one another. The method can thus provide a high-quality film without requiring any precision procedures, skilled techniques or the like.

DESCRIPTION OF EMBODIMENTS

Figure 1:
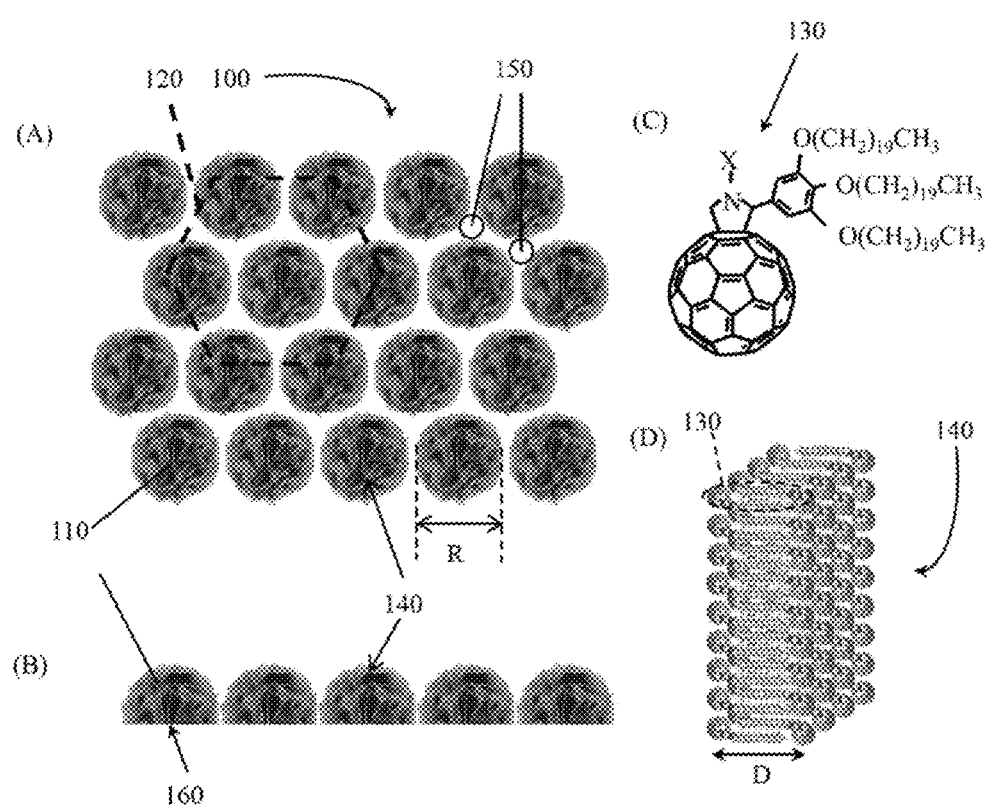
FIG. 1 shows schematic illustrations of a film (A) and (B), a fullerene derivative (C), and a bilayer membrane structure (D) of the present invention.

An embodiment of the present invention is described below with reference to the accompanying drawings. Note that like elements are appended with like reference numerals, and explanations thereof are omitted.

FIG. 1 shows schematic illustrations of a film of the present invention (A) and (B), a fullerene derivative (C), and a bilayer membrane structure (D).

FIG. 1(A) is a diagram representing a film 100 of the present invention as viewed from above (a direction parallel to the flat surface of the film 100). FIG. 1(B) is a diagram representing the film 100 of the present invention as viewed from a cross sectional direction of the film 100.

The film 100 of the present invention is formed of hemispherical particles 110. As used herein, the term "hemispherical particles" is intended to mean structures of a hemispherical or substantially hemispherical form. The hemispherical particles 110 are organized like a hexagonal close-packed structure 120. The hemispherical particles 110 organized like the hexagonal close-packed structure 120 are joined to one another via π-π interactions at the fullerene moieties, and the van der Waals' force of the alkyloxy chains of fullerene derivatives 130 forming the hemispherical particles 110. This makes the film of the present invention highly orderly and stable. It should be noted that the hemispherical particles 110, shown in FIG. 1(A) and (B) as being separated from one another for clarity, are actually joined to and in contact with one another.

As schematically represented in FIG. 1(C), the fullerene derivatives 130 forming the hemispherical particles 110 each include a fullerene moiety, a benzene ring attached to the fullerene moiety, and alkyloxy chains attached to positions 3, 4, and 5 of the benzene ring, and are represented by the following formula (1).

[Chemical Formula 4]

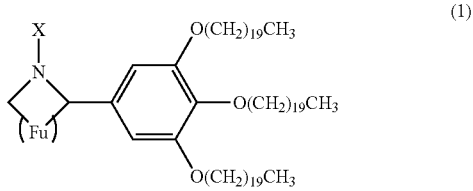

(1)

In the formula, X is a hydrogen atom or a methyl group, and (Fu) is any fullerene, for example, such as $C_{60}$, $C_{70}$, $C_{76}$ and $C_{84}$. Particularly preferred is $C_{60}$, because it has very high $I_h$ symmetry, most stable and least expensive, and can be handled with ease.

In the present invention, the alkyloxy chains at positions 3, 4, and 5 of the benzene ring of the fullerene derivatives 130 each have 20 carbon atoms. From various known fullerene derivatives, the present inventor found that a film of desirable quality can be obtained with the fullerene derivatives 130 represented by the formula (1).

The fullerene derivatives 130 forming the hemispherical particles 110 preferably form a bilayer membrane structure 140 (FIG. 1(D)) as the nanoassembly backbone. As schematically shown in FIG. 1(D), the bilayer membrane structure 140 is a structure in which the fullerene derivatives 130 are arranged to aggregate via the π-π interactions at the fullerene moieties and via the van der Waals' force of the alkyloxy chains at positions 3, 4, and 5 of the benzene ring. The intermembrane distance D in the bilayer membrane structure 140 is 4.5 nm±0.5 nm.

The bilayer membrane structure 140 is assembled so as to provide a flake-like surface for the hemispherical particles 110. More specifically, the hemispherical particles 110 have a flake-like hemispherical surface, and a smooth flat bottom surface. Such a structure can be obtained through self-assembly according to the producing method to be described later. Whether the surface is flake-like or not can easily be determined by electron microscopy or the like. As used herein, the term "flake-like" is intended to mean the randomly assembled state of the bilayer membrane structure 140. For example, in (A) and (B) of FIG. 1, each folded portion in the hemispherical particles 110 as a whole is the bilayer membrane structure 140, and it can be understood that the hemispherical particles 110 are formed by the random assembly of the bilayer membrane structure 140.

The hemispherical particles 110 have excellent monodispersity, and the particle size R ranges from 15 µm to 35 µm, more preferably 20 µm to 30 µm. In these ranges, the hemispherical particles 110 can be organized like a hexagonal close-packed structure, and a film of desirable quality can be obtained over a large area. The particle size R is the diameter of each hemispherical particle 110, and can be determined by analyzing the SEM image.

As described above, the hemispherical particles 110 are configured from the bilayer membrane structure 140 formed by the fullerene derivatives 130. The bilayer membrane structure 140, specifically the fullerene derivatives 130 forming the bilayer membrane structure 140 are distributed in a manner that makes the fullerene derivatives 130 denser at the bottom surface center 160 of the hemispherical particles 110 (the bottom surface center 160 is the center of the flat surface of the hemispherical particles 110) and sparser toward the outer side. In other words, the hemispherical particles 110 can be porous toward the outer side from the bottom surface center 160. This structure is due to the mechanism of nucleation during the film formation according to the producing method described below.

The film 100 shown in FIG. 1 is formed by a single layer formed of the hemispherical particles 110. However, the film 100 may be a multilayer film formed of the hemispherical particles 110.

A process for producing the film 100 of the present invention is described below.

Figure 2:
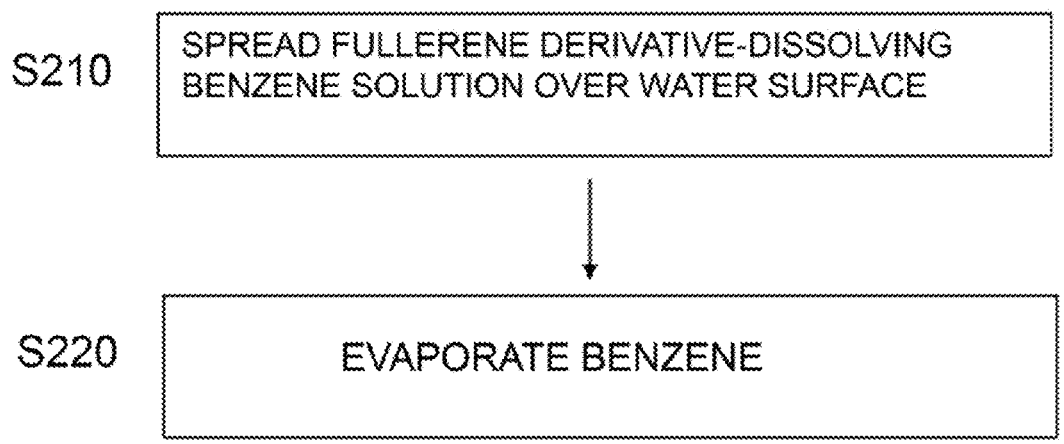
FIG. 2 is a flowchart representing a process for producing the film of the present invention.

FIG. 2 is a flowchart representing a process for producing the film of the present invention.

Figure 3:
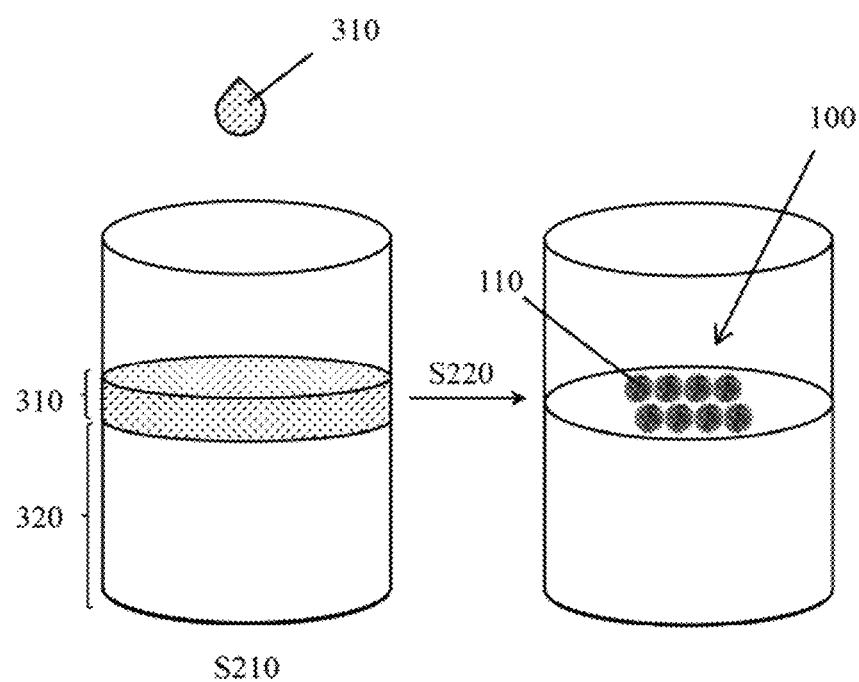
FIG. 3 is a schematic diagram representing a process for producing the film of the present invention.

FIG. 3 is a schematic diagram representing a process for producing the film of the present invention.

Figure 4:
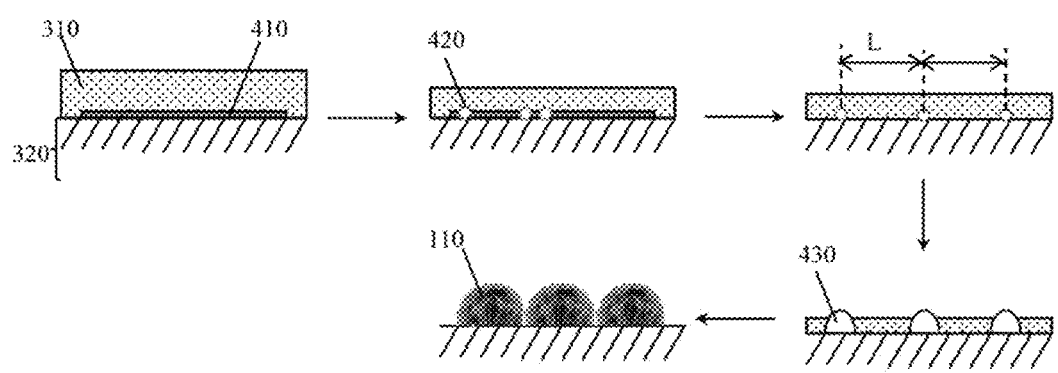
FIG. 4 is a schematic diagram representing the mechanism by which the film of the present invention is formed.

FIG. 4 is a schematic diagram representing the mechanism by which the film of the present invention is formed.

Step S210: A benzene solution 310 (FIG. 3) dissolving fullerene derivatives in benzene is spread over the surface of water 320 (FIG. 3). Here, the fullerene derivatives are the fullerene derivatives represented by the foregoing formula (1). Benzene is a good solvent of fullerene derivatives. An ultrathin film 410 (FIG. 4) formed of the fullerene derivatives can form at the interface between the water surface and the benzene solution.

The amount of the benzene solution spread over the water surface preferably ranges from 13.5 µL to 14.5 µL per 1 $cm^2$ area of the water surface. With the benzene solution spread in 13.5 µL/$cm^2$ or more, the fullerene derivatives can sufficiently exist in the benzene solution, and the hemispherical particle growth can be promoted more effectively. With the benzene solution spread in 14.5 µL/$cm^2$ or less, the fullerene derivatives will not be in excess in the benzene solution, and the hemispherical particles having excellent monodispersity, and the assemble film formed of the hemispherical particles can be formed more effectively to provide a less disordered structure.

The concentration of the benzene solution preferably ranges from 1.5 mM to 2.5 mM. With a benzene solution concentration of 1.5 mM or more, the fullerene derivatives can sufficiently exist in the benzene solution, and the hemispherical particle growth can be promoted more effectively. With a benzene solution concentration of 2.5 mM or less, the fullerene derivatives will not be in excess in the benzene solution, and the hemispherical particles having excellent monodispersity, and the assemble film formed of the hemispherical particles can be formed more effectively to provide a less disordered structure.

Step S220: The benzene in the benzene solution 310 is evaporated. As the benzene evaporates, particle-forming nucleus 420 (FIG. 4) is formed in the ultrathin film 410 obtained in step S210. The nucleus 420 may include the bilayer membrane structure 140. As the benzene evaporates further, a close-pack stable nucleus interval L (FIG. 4) occurs as determined by the centers of the nucleus 420. Because the fullerene derivatives in the benzene solution 310 are constantly supplied to the nucleus 420 as the benzene evaporates, the nucleus 420 grows at the nucleus intervals L as determined. Here, nucleus growth 430 (FIG. 4) proceeds in a planar fashion along the water surface in portions where the nucleus 420 is in contact with the water surface, and spherically in portions where the nucleus 420 is not in contact with water surface (portions in contact with gas). Here, the bilayer membrane structure 140 formed by the fullerene derivatives can randomly assemble to form a flake-like surface. On the other hand, the bilayer membrane structure 140 forms a smooth surface in portions where the nucleus 420 is in contact with the water surface. Nucleus growth continues until the benzene completely evaporates, and the hemispherical particles 110 (FIG. 1 and FIG. 4) are obtained at the completion of the benzene evaporation. All these processes proceed by self-assembly, using the bilayer membrane structure 140 as the nanoassembly backbone.

Because the fullerene derivatives in the benzene solution 310 (FIG. 4) are supplied during the nucleus growth, the concentration of the benzene solution 310 (FIG. 4) decreases as the benzene evaporates. It can therefore be understood that the fullerene derivatives in the hemispherical particles 110, very dense at the initial stages of the nucleus growth, become sparse as the nucleus growth proceeds.

In a specific procedure of benzene evaporation, the benzene solution spread over the water surface (Step S210) is allowed to stand preferably at room temperature (room temperature as used herein ranges from 15° C. to 30° C.) in the dark. In this way, the benzene can slowly evaporate in the constant environment, the monodispersity of the hemispherical particles is excellent, and a film having a hexagonal close-packed structure-like desirable organization can be obtained.

Further, in a specific procedure of benzene evaporation, the benzene solution spread on the water surface (step S210) is preferably allowed to stand under sealed conditions. In this way, rapid evaporation of the benzene can be suppressed, the monodispersity of the hemispherical particles is excellent, and a film having a hexagonal close-packed structure-like desirable organization can be obtained.

An even better quality film can be obtained by evaporating the benzene at room temperature in the dark under sealed conditions. The evaporation time of benzene is, for example, 24 to 48 hours, though it varies depending on factors such as environment, water surface area, and benzene solution amount.

The film 100 formed of the hemispherical particles 110 (FIG. 1) over the water surface can be obtained through steps S210 and S220. Specifically, with the method of the present invention, the hemispherical particles 110 having anisotropic shape are organized like a hexagonal close-packed structure by self-assembly without processes such as heating and recrystallization, and thereby can obtain the film 100 formed of the hemispherical particles 110. The method can thus easily provide the film of the present invention at low cost, with an area in excess of 1 mm$^2$, without requiring any special expensive devices. Further, the method of the present invention simply includes steps S210 and S220, and can provide a high-quality film without requiring any precision procedures, skilled techniques or the like.

Step S230: Following step S220, the film formed of hemispherical particles obtained in step S220 may be transferred to a substrate (not illustrated). The substrate may be any material, including, for example, a silicon substrate, a glass substrate, a plastic substrate, and a metal plate. Further, the substrate may have any surface shape, including, for example, a flat surface, and a spherical surface. In a specific procedure of transferring the film to the substrate, the substrate is simply dipped in the water surface, and the hemispherical particle-arrays are physically adsorbed to the substrate. Here, the film can be adsorbed to the substrate by using the horizontal lifting method or the vertical dipping method (dipping method) used in the Langmuir-Blodgett technique, without varying the surface pressure of the air-liquid interface.

Use of the film 100 (FIG. 1) formed of the hemispherical particles 110 (FIG. 1) of the present invention is described below.

As described above, the film 100 of the present invention is a film formed of the hemispherical particles 110 organized like a hexagonal close-packed structure. The film 100 of the present invention can thus have spaces 150 (FIG. 1) where the hemispherical particles 110 are not in contact with each other. The film 100 of the present invention can be used as a filter by using such spaces 150. Further, semiconductor particles may be supported on the film 100 of the present invention to impart a photocatalytic function. As an example, the semiconductor particles may be titanium dioxide particles. Further, by supporting metal nanoparticles with semiconductor particles, the imparted photocatalytic function can improve. Examples of the metal nanoparticles include platinum, silver, lead, palladium and the like. These particles can easily be supported by using a chemical liquid-phase growth method such as electrolytic or non-electrolytic plating, or a physical vapor deposition method such as sputtering.

Because the film 100 of the present invention is formed of the hemispherical particles 110 having anisotropic shape, for example, different catalytic reactions can take place on the spherical surface side and the flat surface side by attaching different metals to the spherical surface side and the flat surface side of the hemispherical particles 110.

The film 100 of the present invention is formed of the hemispherical particles 110 having a flake-like surface, similar to the assembled structure of fullerene derivatives described in Patent Literature 1. The film 100 of the present invention can thus be expected to have (super)hydrophobicity or photoconductivity as in Patent Literature 1.

With regard to the particle size and the hexagonal close-packed structure-like arrangement of the hemispherical particles 110, the structure of the film 100 of the present invention is reminiscent of the retinal structure of the compound eye of organisms such as flies and mosquitoes. The film 100 of the present invention can thus be used as a mimic of the retinal structure of organisms having the compound eye.

By using the film 100 of the present invention as a template, the retinal structure of organisms having the compound eye can be transferred to a metallic material, a polymer, or an inorganic material. For example, a metallic material with the transferred retinal structure of organisms having the compound eye can be provided by dipping the film 100 of the present invention in a good solvent of the film 100 after attaching a metallic material such as Ag, Pt, Pd, Ti, Ni, and Au to the film 100 of the present invention by using the technique described in JP-A-2009-061580.

The metallic material with the transferred structure has SERS (surface enhanced Raman scattering) activity, SEF (surface enhanced fluorescence) activity, or localized plasmon heating characteristics as decided by the type of the metal used for the metallic material, in addition to the structural characteristics of the film 100 of the present invention. For example, when the metallic material with the transferred structure has SERS activity in addition to the spaces described above, the metallic material with the transferred structure may be used as a filter not only for the filtering of substances but for analyses based on SERS activity.

An insulating layer such as alkanethiol may be attached to the metallic material having the transferred structure, and a TiO$_2$ layer may be attached to the insulating layer. In this way, a material with large specific surface area and facet-dependent catalytic activity can be obtained. Further, when the metallic material used for the structure transfer is Pt or Pd, procedures involving coating of an organic thin film will not be necessary, and the material can be expected to have catalytic activity based on the size of its specific surface area. Alternatively, with some types of metal, the metallic material with the transferred structure can be a conductive filter that takes advantage of the spaces. Such filters have potential as a high-efficient electrolytic electrode.

Figure 5:
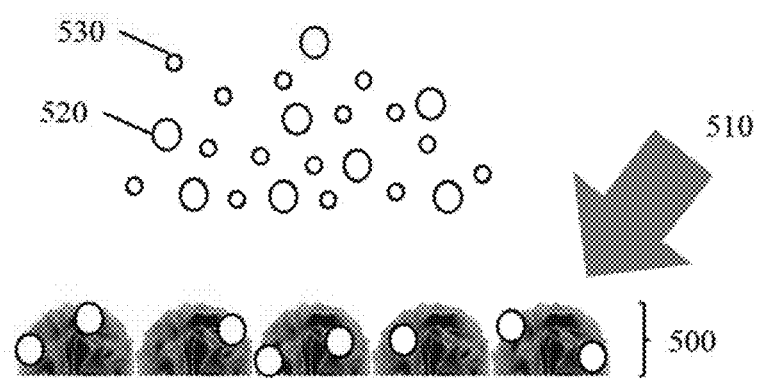
FIG. 5 is a schematic diagram representing a filter that uses the film of the present invention.
Figure 5:
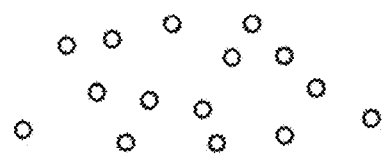

FIG. 5 is a schematic diagram representing a filter that uses the film of the present invention.

A filter 500 includes the film 100 of the present invention, and titanium dioxide particles (not illustrated) and silver particles (not illustrated) attached to the film as semiconductor particles and metal nanoparticles, respectively. The titanium dioxide particles supported by the filter 500 generate reactive oxygen upon irradiation of the filter 500 with light 510. The reactive oxygen acts on a specific substance 520 such as a harmful substance. The specific substance 520 is adsorbed to the filter 500 after being decomposed. On the other hand, a substance 530 not acted upon by the reactive oxygen passes through the filter 500. The filter 500 can thus function as a photocatalytic filter. After the separation, the specific substance 520 may be analyzed by SERS, or may be processed by plasmon heating.

The film 100 of the present invention has a large surface area, because of the hemispherical particles 110 assembled to have a flake-like surface. The film 100 can thus be advantageously used to provide a photocatalytic filter, capable of effectively decomposing and adsorbing the specific substance 520.

The present invention is described below in greater detail using specific examples.

EXAMPLE 1

In Example 1, a benzene solution dissolving fullerene derivative $(3,4,5)C_{20}$-$C_{60}$ (X is a methyl group, and Fu is $C_{60}$ in the formula (1)) in benzene was spread over water (water surface; lower aqueous-phase liquid) to obtain a film of the present invention. A cylindrical glass vial (volume: 10 mL) with the water surface effective area (spread area) of 4.9 cm$^2$ was used. The experiment was conducted in the atmosphere at 22±1° C. under 30 to 35% relative humidity.

The $(3,4,5)C_{20}$-$C_{60}$ was synthesized according to JP-A-2007-137809. The synthesized $(3,4,5)C_{20}$-$C_{60}$ was dissolved in benzene to obtain a 2 mM benzene solution.

The 2 mM benzene solution (70 μL) was spread over the water surface (spread area 4.9 cm$^2$) with a micropipette (step S210 in FIG. 2). Immediately after this procedure, a clear water-benzene solution interface was observed, the water being deionized water having >18 MΩ resistivity. After placing a cap, the vial was allowed to stand at room temperature (22±1° C.) in the dark to evaporate the benzene in the benzene solution (step S220 in FIG. 2). The benzene solution was spread in 14.3 μL per 1 cm$^2$ spread area, and left to stand for 36 hours.

After 36 hours, the water-benzene solution interface disappeared, confirming benzene evaporation. A film, appearing black in color, was observed on the water surface. In order to examine the characteristics of the black film, a washed Si substrate and a washed glass substrate were dipped in a glass vial, and the film was transferred onto the Si substrate and the glass substrate (step S230). The Si substrate and the glass substrate measured 1×1 cm$^2$ in size.

In order to confirm that the film includes hemispherical particles organized like a hexagonal close-packed structure, the film transferred onto the Si substrate was observed by scanning electron microscopy (SEM), for which an XL30 electron microscope (Phillips) was used at an accelerating voltage of 3 kV. The SEM sample was prepared by sputtering Au on the film transferred to the Si substrate, using an automatic sputtering coater (JFC-1300, JEOL Ltd.) equipped with an MTM-20 thickness controller. The results are presented in FIGS. 6 and 8. For comparison, the results of the observation of the compound eye structures of mosquito and ant are presented in FIG. 7. The film on the Si substrate was observed under a 3D laser confocal microscope (OLS4000, Shimadzu Corporation). The observation results are shown in FIG. 9.

Figure 10:
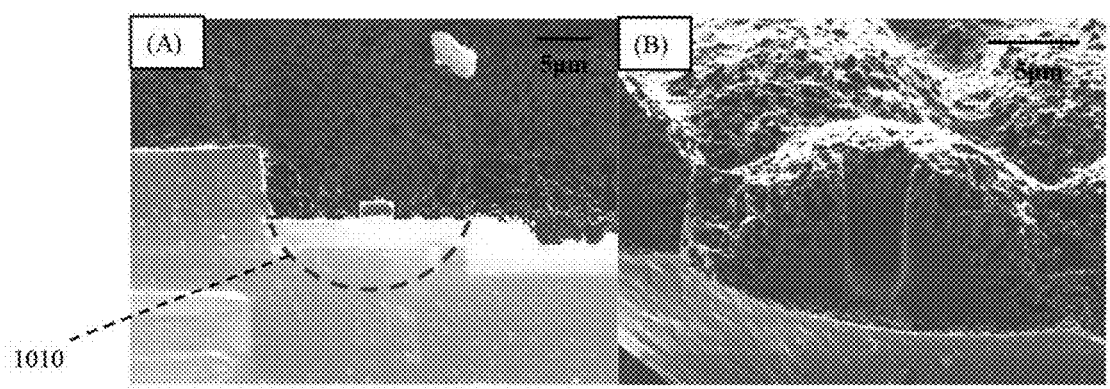
FIG. 10 shows SIM images of the film produced in Example 1.

A part of the film transferred onto the Si substrate was attached to a conductive tape, and observed with a focusing ion beam sample fabrication device (JEM-9310FIB, JEOL Ltd.). For the confirmation of a film cross section, the film was cut with a focused ion beam (FIB). The accelerating voltage was 20 kV. A scanning electron microscope JSM-6700F (JEOL) was used for the cross section observation. The accelerating voltage was 20 kV. The results are shown in FIG. 10.

In order to confirm that the film was the fullerene structure that uses the bilayer membrane structure as the nanoassembly backbone, the film on the Si substrate was identified by powder X-ray diffraction (XRD), and a part of the film was observed by high-resolution cryogenic transmission electron microscopy (HR-cryo-TEM). XRD was performed with an X-ray diffractometer (Nanostar SAXS system, Bruker AXS) using monochromatic Cu Kα rays (λ=0.15405 nm) produced with a monochrometer. The result is presented in FIG. 11.

Figure 12:
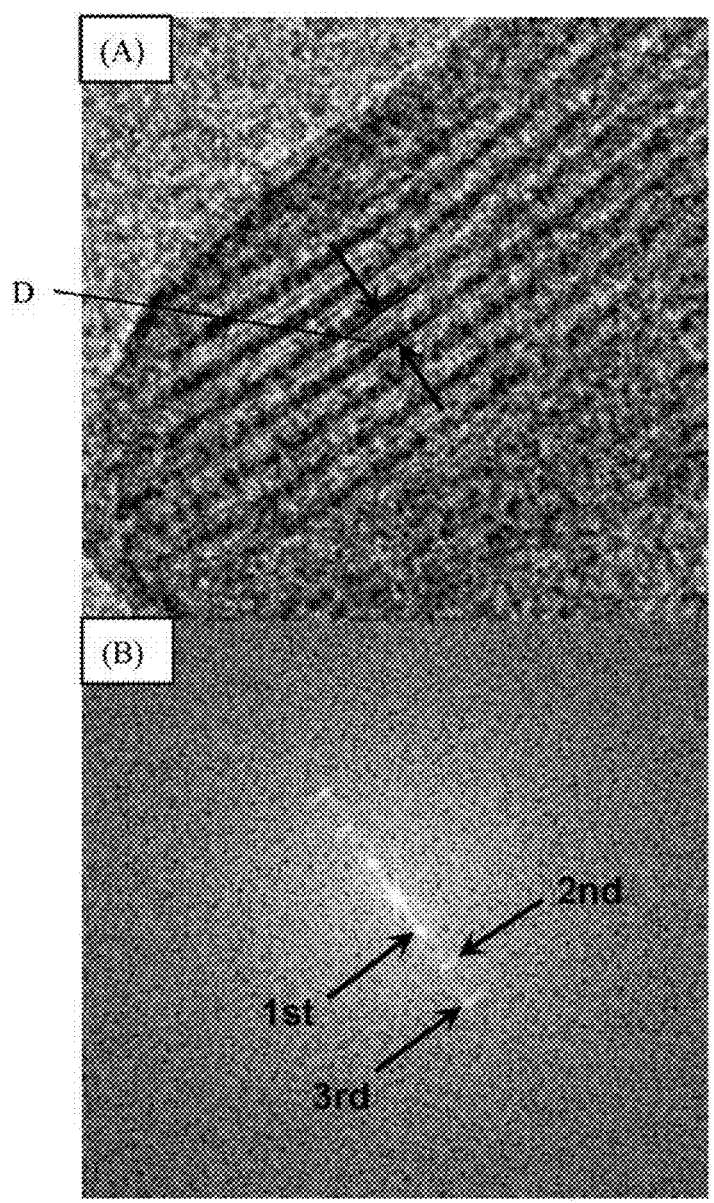
FIG. 12 shows a TEM image (A) and Fourier transformation (FFT) pattern (B) of the film produced in Example 1.

HR-cryo-TEM observation was performed with a transmission electron microscope (JEM-2100F(G5), JEOL Ltd.) under an accelerating voltage of 400 kV. The HR-TEM sample was prepared as follows. A solution of the film dispersed in alcohol after being pulverized and powdered was dropped onto a carbon grid, and the excess solution on the grid was removed with a filter paper. The observation results are shown in FIG. 12.

EXAMPLE 2

In Example 2, the film forming process of the film obtained in Example 1 was examined by spreading the benzene solution of the $(3,4,5)C_{20}$-$C_{60}$ of Example 1 over water (water surface; lower aqueous-phase liquid) in various concentrations and amounts. Note that, in Example 2, the concentrations and the amounts of the benzene solution are selected for the purpose of examining the film forming process, and do not necessarily fall within the foregoing preferable ranges.

The benzene solution was spread over the water surface (spread area 4.9 cm$^2$) in the following concentrations and amounts.

1 mM, 25 μL
1 mM, 45 μL
1 mM, 55 μL
2 mM, 25 μL
2 mM, 45 μL
2 mM, 60 μL
2 mM, 70 μL

Figure 13:
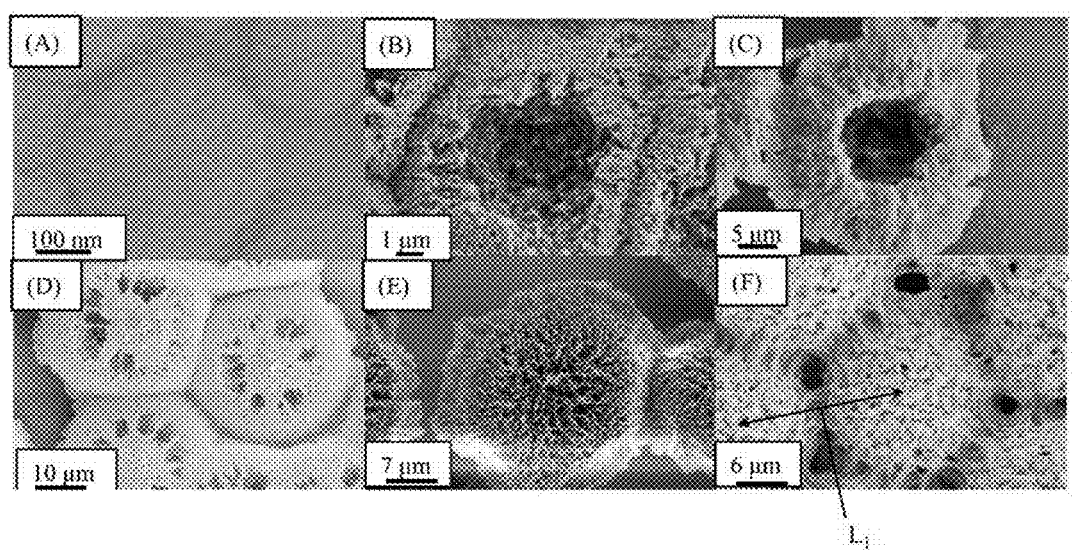
FIG. 13 shows SEM images of the films produced in Example 2.

The other conditions are the same as those used in Example 1. Each film obtained as above was transferred onto a Si substrate, and observed under SEM as in Example 1. The results are shown in FIG. 13.

Figure 14:
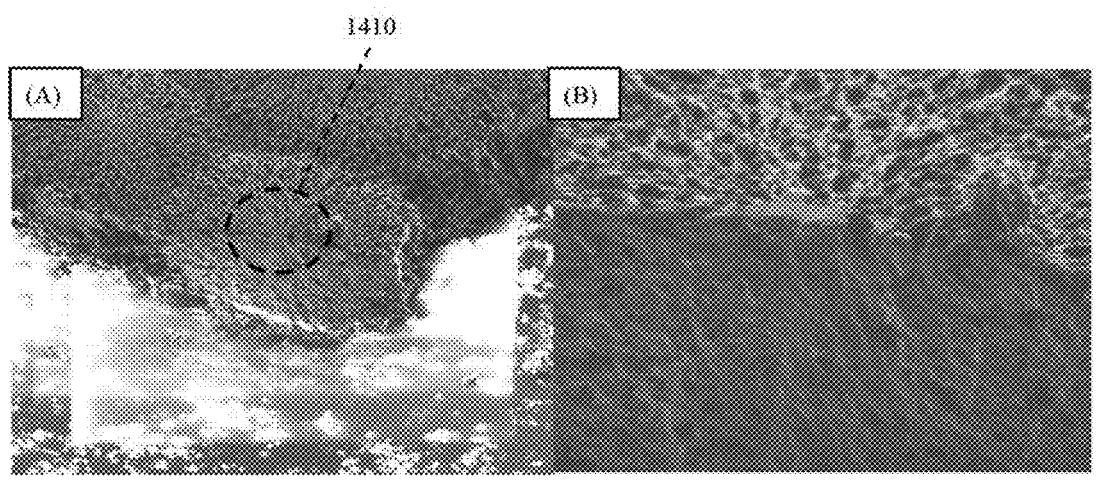
FIG. 14 shows SIM images of the film produced in Example 2.

The film obtained from the benzene solution spread in a concentration of 2 mM and an amount of 70 μL was observed under SIM as in Example 1. The result is shown in FIG. 14.

EXAMPLE 3

Figure 15:
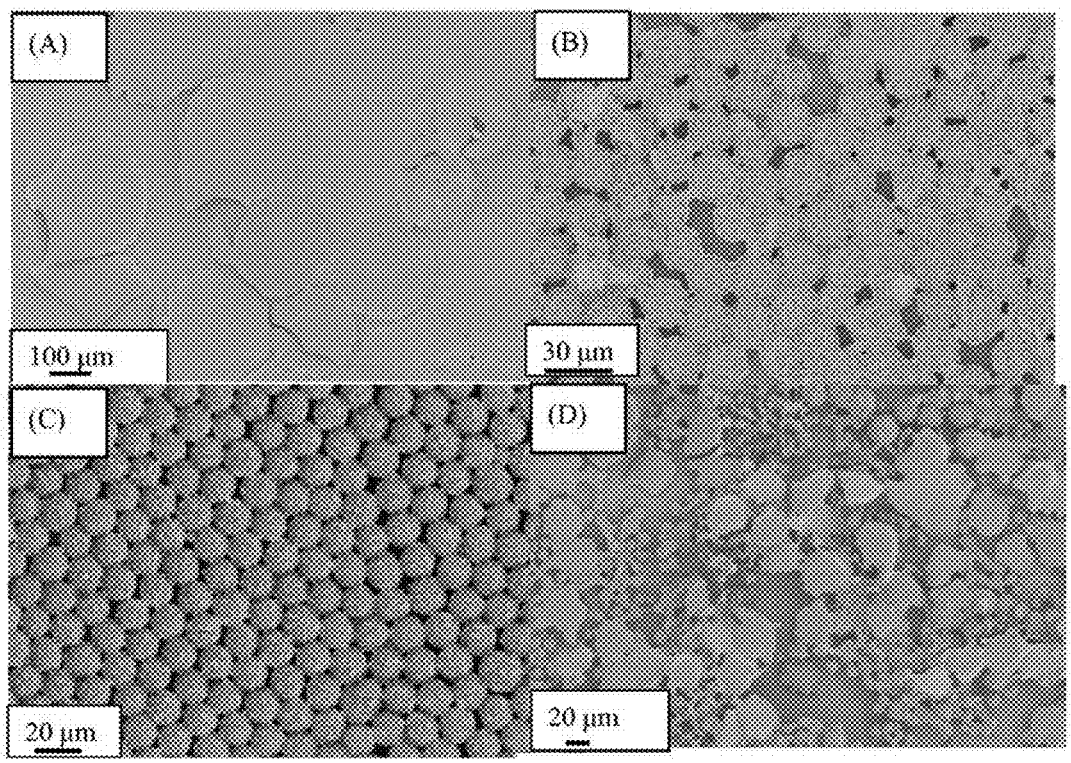
FIG. 15 shows SEM image of the films produced in Example 3.

In Example 3, the fullerene derivative-containing solution spread over the lower aqueous phase was examined for amount dependence. The procedures were the same as in Example 1, except that the spread amount was changed from 70 μL to 20 μL, 40 μL, and 100 μL. Each film was transferred onto a Si substrate, and observed under SEM as in Example 1. The results are shown in FIG. 15. The benzene solution (20

μL, 40 μL, and 100 μL) were spread in 4.1 μL, 8.2 μL, and 20.4 μL, respectively, per 1 cm² spread area.

COMPARATIVE EXAMPLE 1

Figure 16:
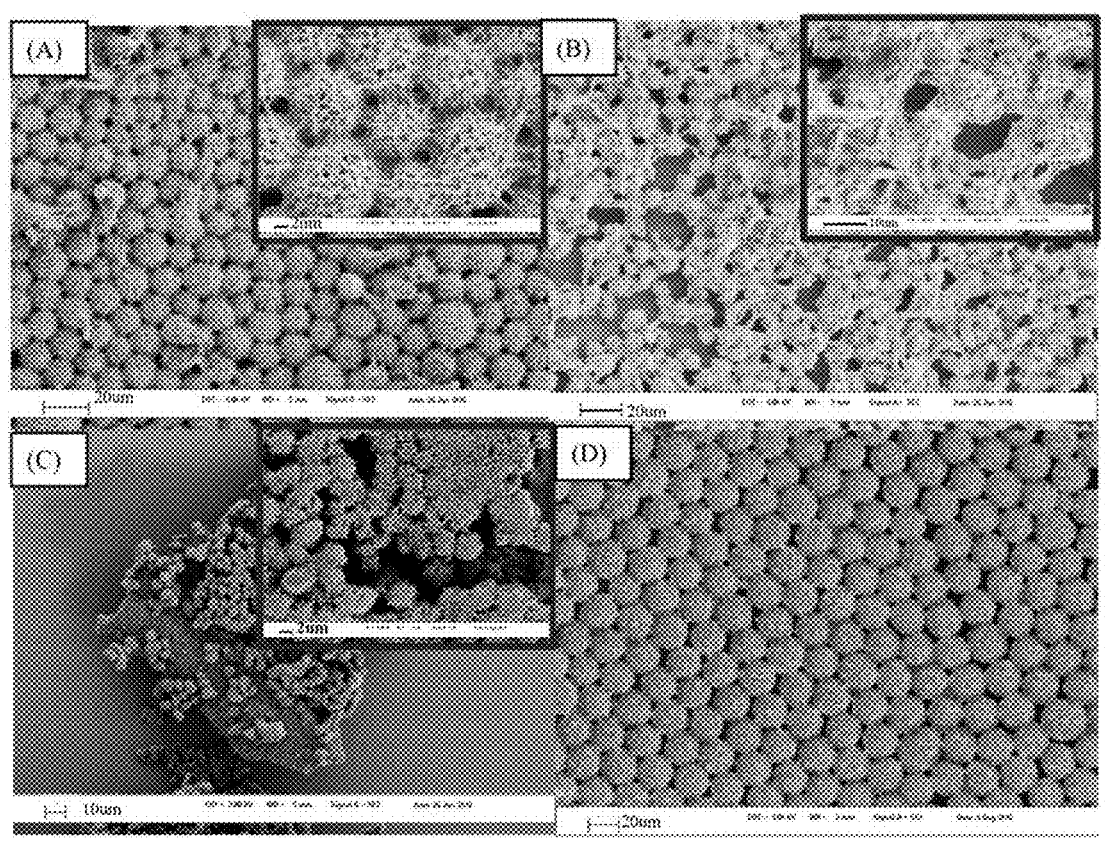
FIG. 16 shows SEM images of the films produced in Comparative Example 1.

In Comparative Example 1, lower aqueous phase-dependence was examined. The procedures were the same as in Example 1, except that the lower aqueous phase was changed from water to a mixed solution of methanol and water, a mixed solution of ethanol and water, and a mixed solution of propanol and water. The mixed ratio of each alcohol to water was 1:4 (volume ratio) in all samples. Each film was transferred onto a Si substrate, and observed under SEM as in Example 1. The results are shown in FIG. 16.

COMPARATIVE EXAMPLE 2

Figure 17:
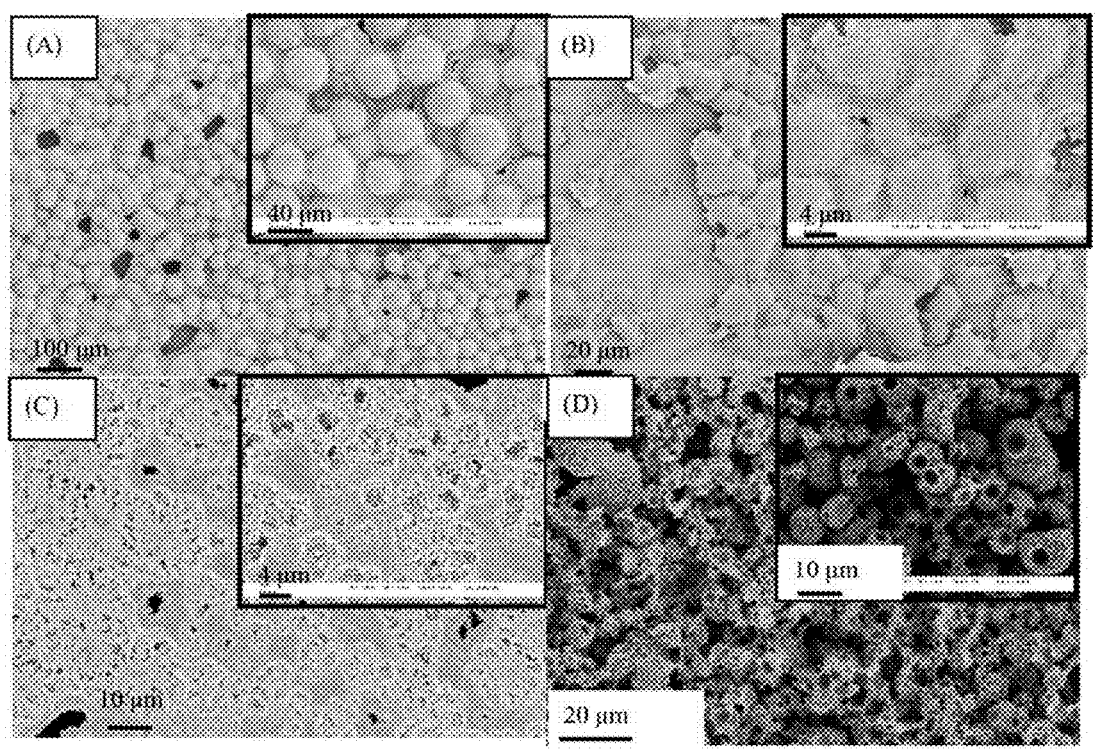
FIG. 17 shows SEM images of the films produced in Comparative Example 2.

In Comparative Example 2, fullerene derivative-containing solvent-dependence was examined. The procedures were the same as in Example 1, except that the solvent was changed from benzene to toluene, dichloromethane ($CH_2Cl_2$), chloroform ($CHCl_3$), and m-xylene. Each film was transferred onto a Si substrate, and observed under SEM as in Example 1. The results are shown in FIG. 17.

COMPARATIVE EXAMPLE 3

Figure 18:
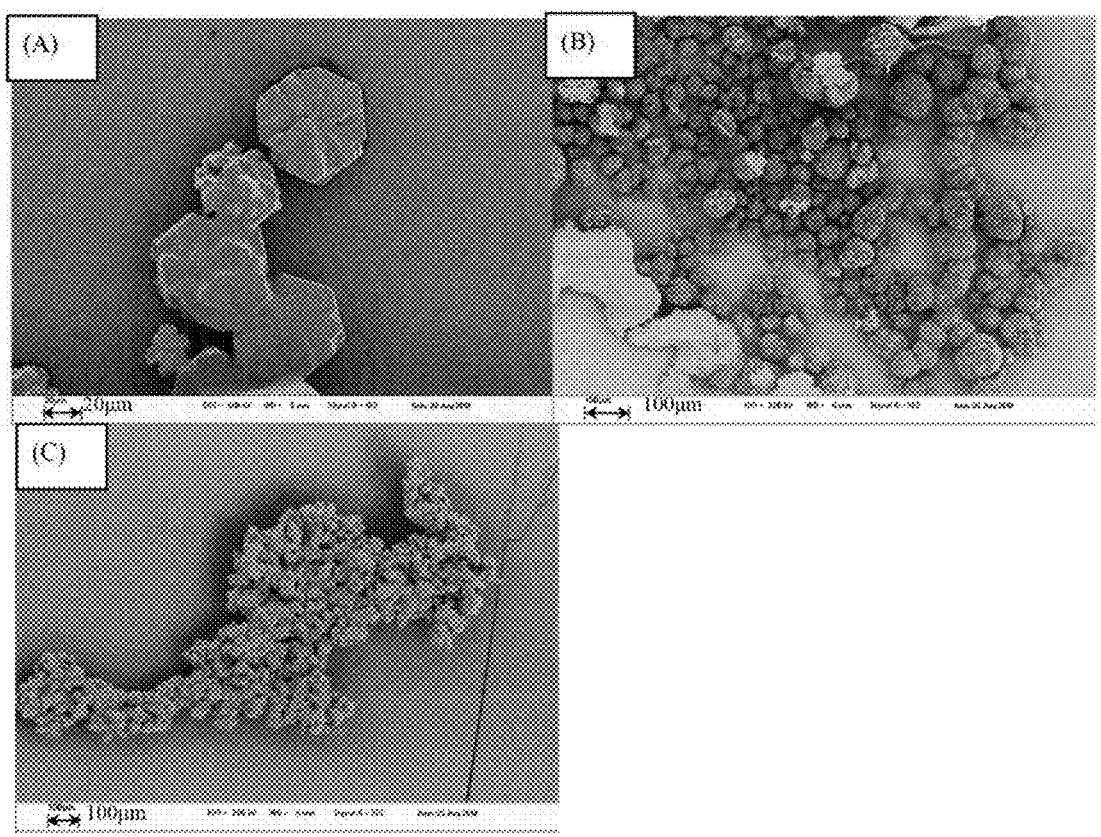
FIG. 18 shows SEM images of the films produced in Comparative Example 3.

In Comparative Example 3, film formation was examined for its dependence on the type of the solute contained in the spread solution. The procedures were the same as in Example 1, except that the solute was changed from $(3,4,5)C_{20}$-$C_{60}$ to $C_{60}$, $(3,4)C_{20}$-$C_{60}$, and $(3,4,5)C_{16}C_{60}$. The $C_{60}$ (purity 99.9%) was purchased from Aldrich. The $(3,4)C_{20}$-$C_{60}$ and $(3,4,5)C_{16}C_{60}$ were synthesized according to JP-A-2007-137809. Each film was transferred onto a Si substrate, and observed under SEM as in Example 1. The results are shown in FIG. 18.

EXAMPLE 4

In Example 4, the evaporation conditions of producing the film of the present invention, and the appearance at the early stages of the film production were confirmed. In Example 4, the same fullerene derivatives used in Example 1 were used, and the concentration and the spread amount of the benzene solution were 1 mM and 20 to 30 μL, respectively. The samples were allowed to stand for 30 min without sealing the vial (a circular PTFE Langmuir trough with an effective area of 176 cm²). The film was obtained after being compressed at a barrier speed of 5 cm²/min. The other conditions are the same as in Example 1. Of note, for the confirmation of the appearance in the early stages, the concentration (1 mM) and the spread amount (0.11 μL/cm² to 0.17 μL/cm²) of the benzene solution in Example 4 were set far below the foregoing preferable ranges (1.5 mM to 2.5 mM, and 13.5 μL/cm² to 14.5 μL/cm²), and a much shorter waiting time than the preferable waiting time (24 hours to 48 hours) was set.

Figure 19:
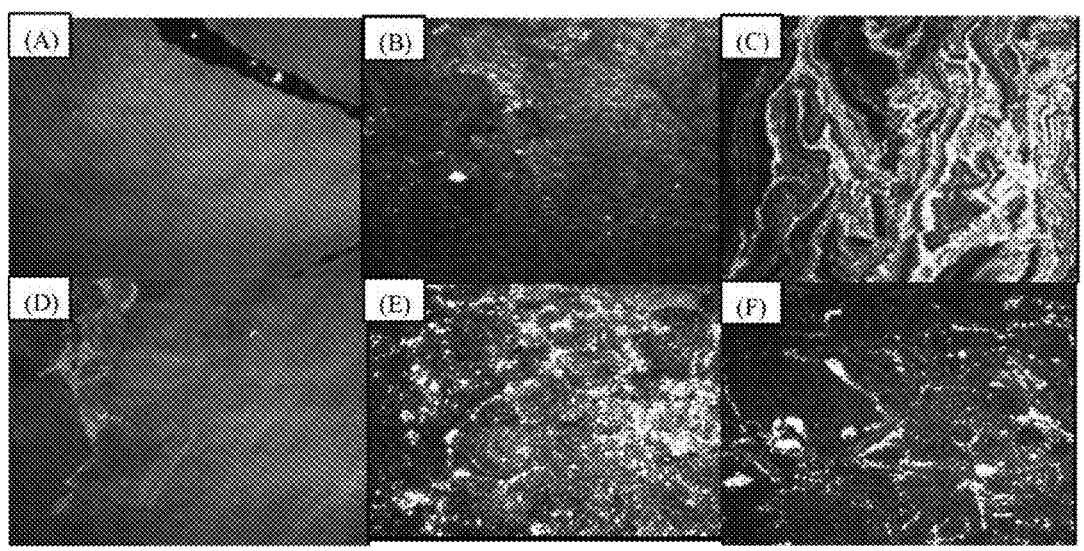
FIG. 19 shows BAM images of the films produced in Example 4 and Comparative Example 4.
Figure 20:
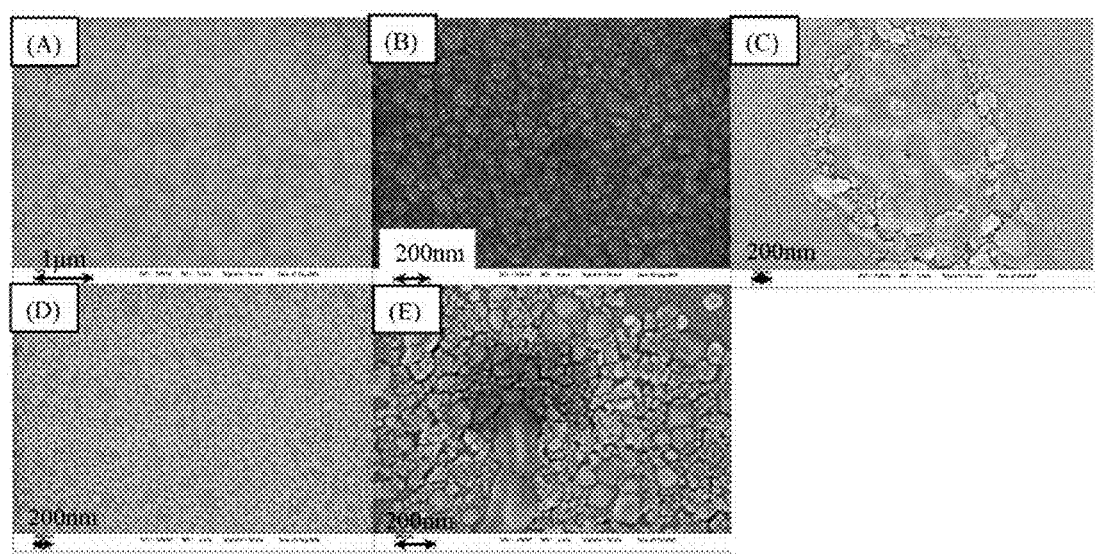
FIG. 20 shows SEM images of the films produced in Example 4 and Comparative Example 4.

The film obtained as above was observed in situ with a Brewster angle microscope (BAM; I-Elli2000; Accurion). A Nd:YAG diode laser (wavelength 532 nm) was used as the light source, and the observation was made at 50 mW laser output. The BAM lateral resolution was 2 μm. The observation results are shown in FIG. 19. The film was then transferred onto a Si substrate, and observed under SEM as in Example 1. The results are shown in FIG. 20.

A surface pressure-molecular area isothermal curve was plotted. The surface pressure was measured by using a Wilhelmy balance with a filter paper plate. The results are presented in FIG. 21. The thin film formed at the air-liquid interface after the benzene evaporation was subjected to ultraviolet-visible spectroscopy (UV-Vis). The UV-Vis reflection spectral measurements were taken at various time points with Nanofilm Surface Analysis Spectrophotometer (Ref-SPEC2, Accurion) after the benzene solution was spread. The UV-vis reflection spectrum was determined from the differences in the refractive indices (ΔR) of the film on the water surface and the water surface without the film for perpendicularly incident light. The results are presented in FIG. 22.

The films obtained at various surface pressures were subjected to infrared reflection absorption spectroscopy (IRRAS). The IRRAS spectral measurements were taken by in situ measurements at the air-liquid interface with a FTIR spectrophotometer (IFS66, Bruker) equipped with a liquid nitrogen cooled MCT (mercury cadmium terbium) detector. The focal point of the infrared rays was set at a 40° angle relative to the film and the lower aqueous phase water (with respect to the normal vector). The resulting signals were normalized against the signals from the lower aqueous phase water to remove the water vapor signals. Note that the IR spectra were collected at 8 cm$^{-1}$ resolution in 200 scans for s-polarized light and 400 scans for p-polarized light. The results are presented in FIG. 24.

COMPARATIVE EXAMPLE 4

In Comparative Example 4, the same procedures used in Example 4 were performed, except that the solvent was changed from benzene to toluene, dichloromethane ($CH_2Cl_2$), chloroform ($CHCl_3$), m-xylene, and p-xylene. Each film was subjected to Brewster angle microscope observation, SEM observation, and UV-Vis and FT-IR measurements as in Example 4. The results are presented in FIGS. 19 to 21, and FIGS. 23 and 25.

The conditions used in Examples and Comparative Examples are summarized in Table 1. The results are described below.

TABLE 1

Deposition conditions of Examples and Comparative Examples

| Ex./Com. Ex. | Lower aqueous phase liquid | Solute | Solvent | Amount (μL) and concentration (mM) of solute-containing solution | Amount of solute-containing solution added per area (1 cm²) of lower aqueous phase (μL) | Solvent evaporation conditions |
|---|---|---|---|---|---|---|
| Ex. 1 | Water | $(3,4,5)C_{20}$-$C_{60}$ | Benzene | 70 μL, 2 mM | 14.3 | Sealed, dark, 36 h |
| Ex. 2 | Water | $(3,4,5)C_{20}$-$C_{60}$ | Benzene | 25 μL/45 μL/ 55 μL, 1 mM | 5.1-14.3 | Sealed, dark, 36 h |

TABLE 1-continued

Deposition conditions of Examples and Comparative Examples

| Ex./Com. Ex. | Lower aqueous phase liquid | Solute | Solvent | Amount (μL) and concentration (mM) of solute-containing solution | Amount of solute-containing solution added per area (1 cm$^2$) of lower aqueous phase (μL) | Solvent evaporation conditions |
|---|---|---|---|---|---|---|
| Ex. 3 | Water | $(3,4,5)C_{20}$-$C_{60}$ | Benzene | 25 μL/45 μL/ 60 μL/70 μL, 2 mM<br>20 μL, 2 mM<br>40 μL, 2 mM<br>100 μL, 2 mM | 4.1, 8.2, 20.4 | Sealed, dark, 36 h |
| Ex. 4 | Water | $(3,4,5)C_{20}$-$C_{60}$ | Benzene | 20-30 μL, 1 mM | 0.11-0.17 | Open, dark, 0.5 h |
| Com. Ex. 1 | MeOH/Water (1:4)<br>EtOH/Water (1:4)<br>PrOH/Water (1:4) | $(3,4,5)C_{20}$-$C_{60}$ | Benzene | 70 μL, 2 mM | 14.3 | Sealed, dark, 36 h |
| Com. Ex. 2 | Water | $(3,4,5)C_{20}$-$C_{60}$ | Toluene<br>m-Xylene<br>$CHCl_3$<br>$CH_2Cl_2$ | 70 μL, 2 mM | 14.3 | Sealed, dark, 36 h |
| Com. Ex. 3 | Water | $C_{60}$<br>$(3,4)C_{20}$-$C_{60}$<br>$(3,4,5)C_{16}$-$C_{60}$ | Benzene | 70 μL, 2 mM | 14.3 | Sealed, dark, 36 h |
| Com. Ex. 4 | Water | $(3,4,5)C_{20}$-$C_{60}$ | Toluene<br>m-Xylene<br>p-Xylene<br>$CHCl_3$<br>$CH_2Cl_2$ | 20-30 μL, 1 mM | 0.11-0.17 | Open, dark, 0.5 h |

Figure 6:
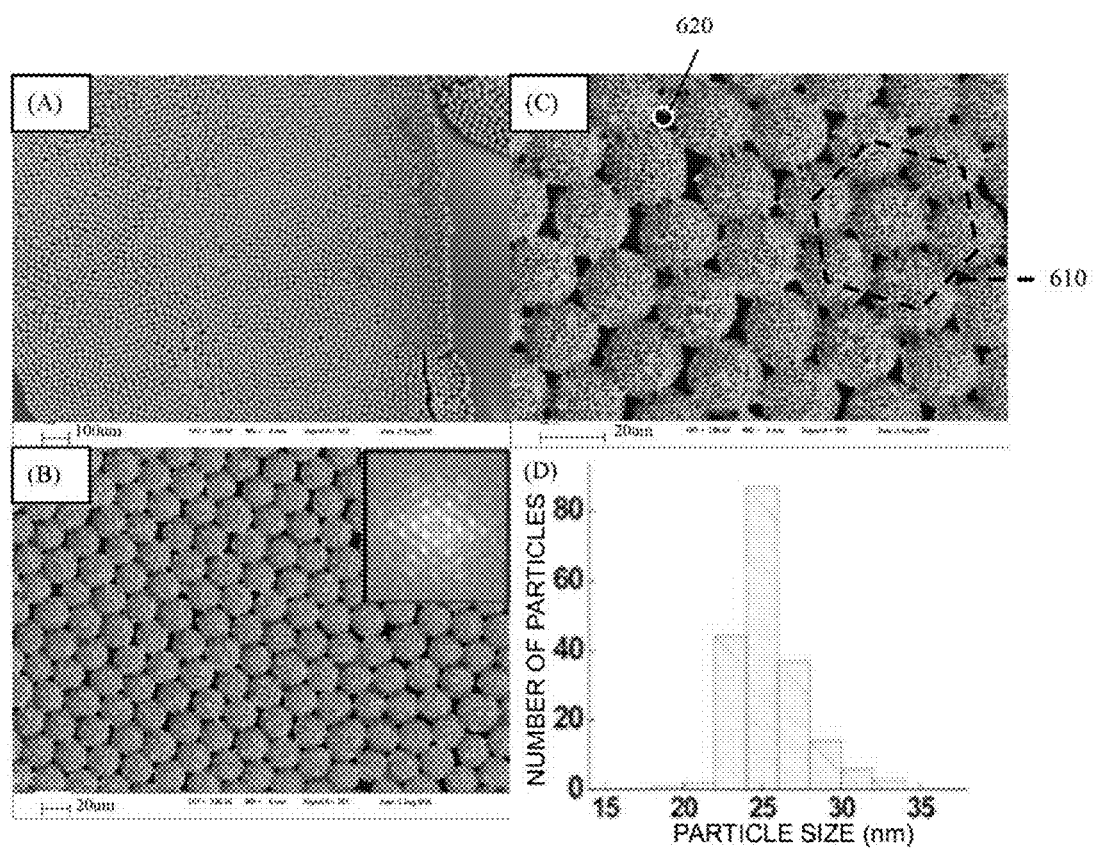
FIG. 6 shows diagrams schematically representing SEM images and the particle size distribution of the film produced in Example 1.

FIG. 6 shows diagrams schematically representing SEM images and the particle size distribution of the film produced in Example 1.

FIG. 6(A) to (C) show SEM images of the film produced in Example 1 captured at various magnifications. FIG. 6(D) is a histogram representing the particle size distribution. The particle size distribution was obtained by analyzing the SEM images. Specifically, the diameters of at least 1,000 particles were measured, and the mean value of the measured diameters was obtained. As can be seen in FIG. 6(A), the film produced in Example 1 was found to be a macroscopic, millimeter-size film of the arranged particles. As can be seen in FIG. 6(B), the film produced in Example 1 was found to be a film of the orderly arranged particles. The inset in FIG. 6(B) shows Fourier transformation (FFT) pattern, indicating that the film has excellent particle monodispersity. Further, as can be seen in FIG. 6(C), the film produced in Example 1 was found to be a film of particles joined to each other in a hexagonal close-packed structure-like organization 610. Spaces 620 were observed in regions where the particles were not in contact with one another. The particle surface (where it did not contact the water surface during the production) was flake-like.

As can be seen in FIG. 6(D), the particle size distribution ranged from 15 μm to 35 μm, particularly 20 μm to 30 μm centered around 25 μm. The mean value of particle size was 25.5±2.4 μm. From these results, it was found that a film formed of particles desirably organized like a hexagonal close-packed structure could be obtained when the size of the particles in the film of the present invention fell in the range of 20 μm to 30 μm.

Figure 7:
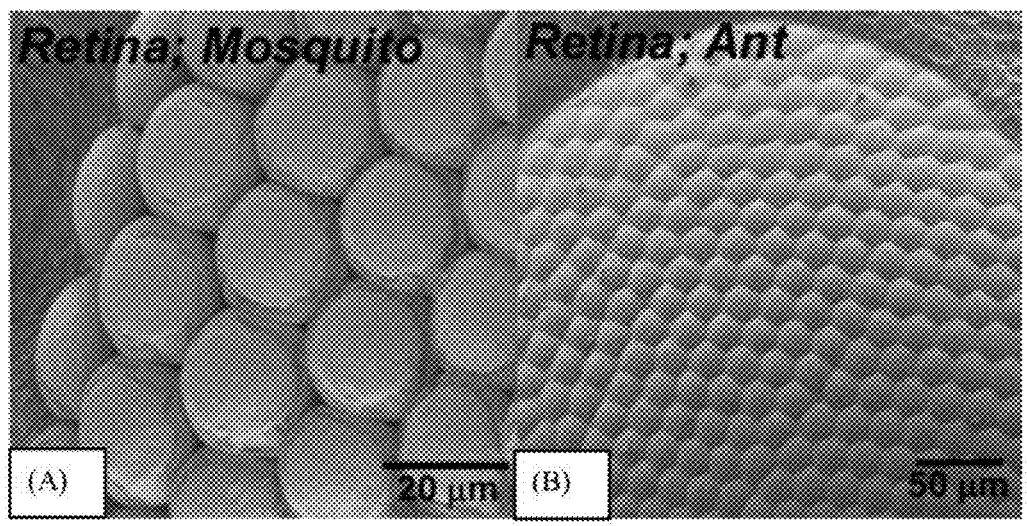
FIG. 7 shows diagrams representing SEM images of mosquito and ant compound eyes.

FIG. 7 shows diagrams representing SEM images of mosquito and ant compound eyes.

FIGS. 7(A) and (B) show compound eyes of mosquito and ant, respectively. By comparing FIG. 6 and FIG. 7, the film of the present invention was found to be very reminiscent of the mosquito and ant compound eyes in particle size and hexagonal close-packed structure-like organization. It was therefore found that the film produced in Example 1 had the retinal structure of the compound eyes of organisms such as mosquitoes and ants.

Figure 8:
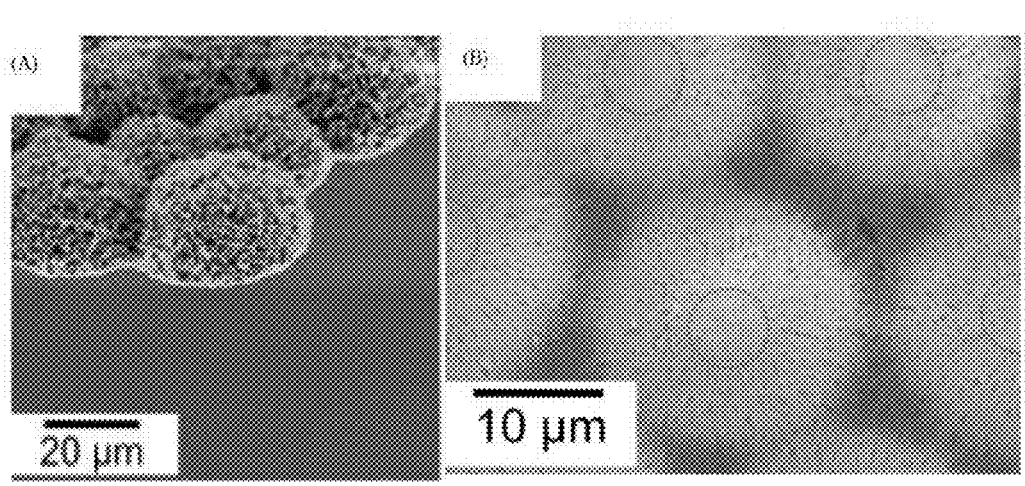
FIG. 8 shows another set of SEM images of the film produced in Example 1.
Figure 9:
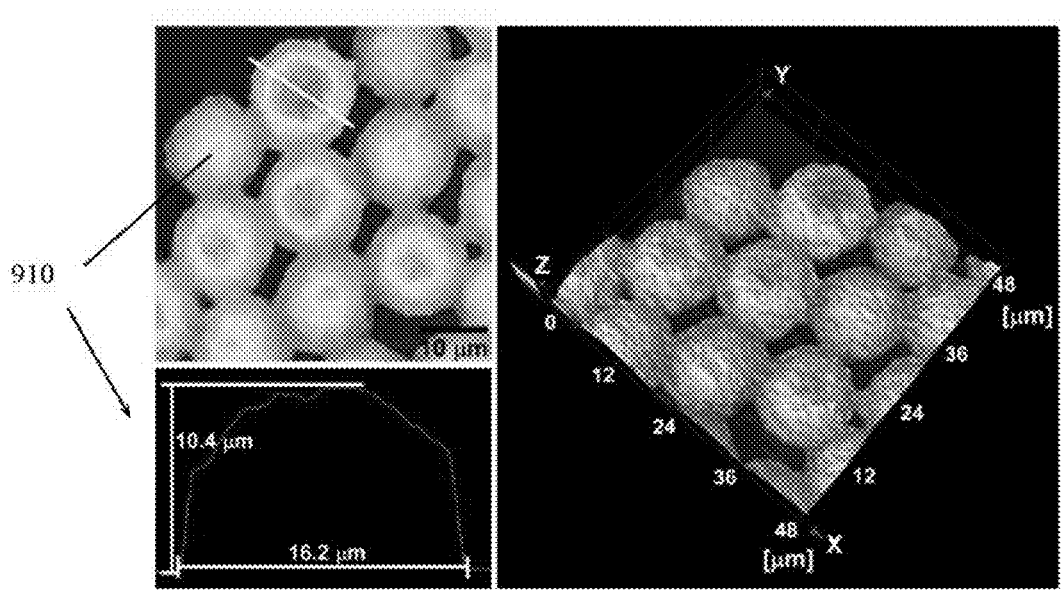
FIG. 9 shows 3D laser confocal microscope images of the film produced in Example 1.

FIG. 8 shows another set of SEM images of the film produced in Example 1.

FIG. 8(A) is a view of the film produced in Example 1 as observed from the side surface, and FIG. 8(B) from the back side. For the observation of the back side, the film formed on the water surface was immobilized on a silicon substrate by using the horizontal deposition procedure. As can be seen in FIGS. 8(A) and (B), the particles observed in FIG. 6 were hemispherical particles.

As can be seen in FIG. 8(B), the bottom surfaces of the hemispherical particles (portions that contact the water surface during the production) were found to be smoother than the hemispherical surfaces of the hemispherical particles (for example, portions that do not contact the water surface during the production (FIG. 6(C)). As demonstrated above, the film of the present invention differs in morphology for the top surface (the hemispherical surface side of the hemispherical particles) and the lower surface (the bottom surface side of the hemispherical particles), and these film surfaces can be used for different purposes. For example, the top surface of the film can preferably be used as a filter surface, because it is flake-like and has a large specific surface area.

FIG. 9 shows 3D laser confocal microscope images of the film produced in Example 1.

In FIG. 9, higher hemispherical particles appear brighter than lower hemispherical particles. Referring to FIG. 9, the hemispherical particles 910 forming the film produced in Example 1 had a particle size of 16.2 μm, and a height of 10.4 μm. Note that even though the particle size presented in FIG.

9 falls within the particle size distribution described with reference to FIG. 6, it is not the value of average particle size, and depends on the measurement point (hemispherical particles).

FIG. 10 shows SIM images of the film produced in Example 1.

FIG. 10(A) is a view of the film produced in Example 1 as viewed from the substrate side. FIG. 10(B) shows a cross section of the region 1010 of FIG. 10(A) taken by FIB. As can be seen in FIG. 10(B), inside of the hemispherical particles was not hollow but dense. More specifically, the hemispherical particles were denser at the center of the bottom surface of the hemispherical particles and sparser toward the outer side. Because the hemispherical particles were formed by the fullerene derivative $(3,4,5)C_{20}$-$C_{60}$, it was confirmed that the fullerene derivative distribution was denser at the bottom surface center and sparser toward the outer side.

Figure 11:
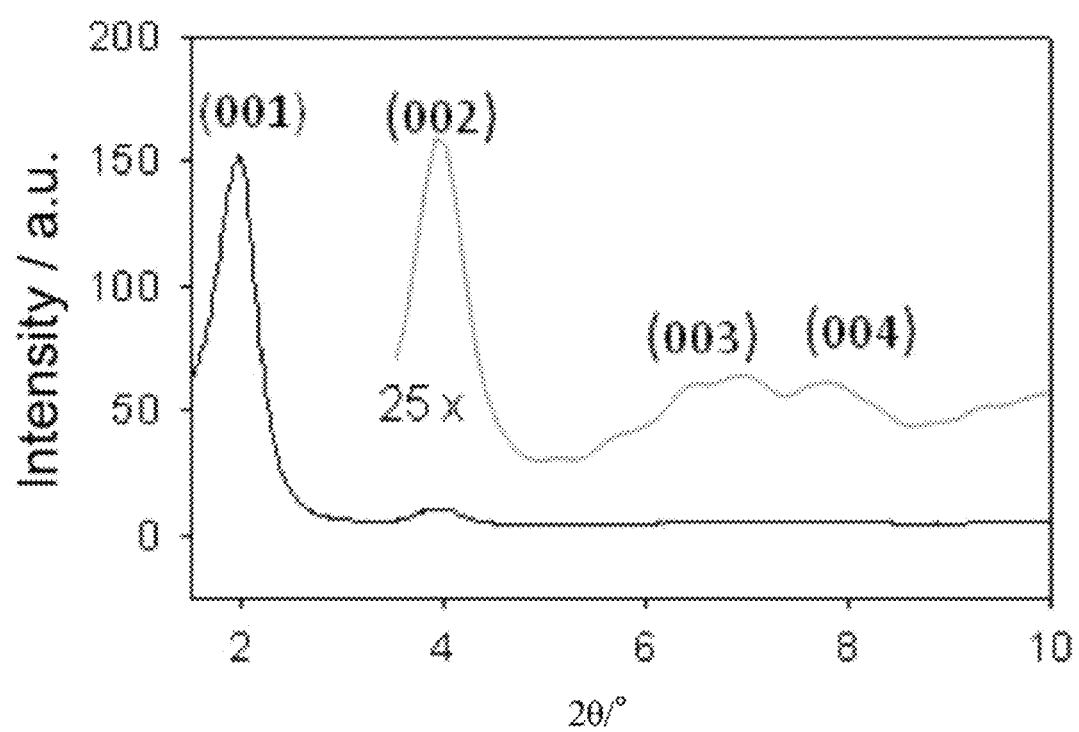
FIG. 11 is a diagram representing X-ray diffraction patterns of the film produced in Example 1.

FIG. 11 is a diagram representing X-ray diffraction patterns of the film produced in Example 1.

Referring to FIG. 11, diffraction peaks (001), (002), (003), and (004) were obtained for the film produced in Example 1. This indicates that the film has an orderly multilayer structure over a long distance. The interlayer distance obtained from FIG. 11 was 4.4 to 4.5 nm. The interlayer distance corresponds to distance D of FIG. 1(D) (the length of the alkyl chains of formula (1) interdigitated to one another).

FIG. 12 shows a TEM image (A) and Fourier transformation (FFT) pattern (B) of the film produced in Example 1.

As can be seen in FIG. 12(A), the film produced in Example 1 was found to have a multilayer bilayer membrane structure (multilamellar structure) and an interlayer distance D of 4.5 nm. This result is in good agreement with the interlayer distance found in FIG. 11. As can be seen in FIG. 12(B), the multilayer structure was found to be highly orderly, as evidenced by the appearance of the third-order spot in FFT.

Referring to FIGS. 11 and 12, by considering that the molecular length of the fullerene derivative $(3,4,5)C_{20}$-$C_{60}$ is about 3.6 nm, the results suggest that the hemispherical particles have the bilayer membrane structure 140 (FIG. 1(D)).

As demonstrated above, it was confirmed from FIGS. 6 to 12 that the film of the present invention was a film formed of hemispherical particles organized like a hexagonal close-packed structure, and that the nanoassembly backbone of the hemispherical particles was the bilayer membrane structure formed by the fullerene derivatives of the formula (1) as schematically illustrated in FIGS. 1(A) and (B). It was also confirmed that the hemispherical particles were assembled to have a flake-like surface. Further, it was demonstrated that the method of the present invention represented in FIG. 2 was the preferred method of producing the film.

FIG. 13 shows SEM images of the films produced in Example 2.

FIG. 13(A) to (F) represent SEM images of the films produced from the benzene solution spread onto the water surface in various concentrations and amounts (1 mM, 25 μL; 1 mM, 45 μL; 1 mM, 55 μL; 2 mM, 25 μL; 2 mM, 45 μL; and 2 mM, 60 μL).

It was confirmed from FIG. 13(A) to (F) that the hemispherical particle growth proceeds with increasing quantities (the concentration or the amount of benzene solution added) of the fullerene derivative $(3,4,5)C_{20}$-$C_{60}$ in the benzene solution.

Specifically, the film of FIG. 13(A) was an ultrathin film 410 (FIG. 4) accompanied by nucleus 420 (FIG. 4). The films of FIGS. 13(B) and (C) underwent nucleus growth 430 (FIG. 4) in a planar fashion along the water surface where the nucleus 420 contacted the water surface, and spherically in portions where the nucleus 420 did not contact the water surface. FIG. 13(D) to (F) show how grain growth proceeded at the maintained close-pack stable nucleus interval $L_1$ (corresponds to L in FIG. 4; determines the final particle size). In Example 2, $L_1$ is 18 μm, and the nucleus interval $L_1$ was found to fall within the particle size distribution range described with reference to FIG. 6.

Referring to FIG. 13(B) to (F) showing hemispherical particle formation by grain growth, it can be seen that the outer side of the hemispherical particles is less dense than the bottom surface center of the hemispherical particles. This result is in good agreement with the result presented in FIG. 10 of Example 1. Though not shown in FIG. 13, the SEM image of the film (2 mM, 70 μL) produced in Example 2 was similar to that shown in FIG. 6 (Example 1).

FIG. 14 shows SIM images of the film produced in Example 2.

The SIM images shown in FIGS. 14(A) and (B) are the FIB cross sectional images of the film produced form the benzene solution spread over the water surface in 2 mM and 70 μL. FIG. 14(B) is a magnified view of the region 1410 of FIG. 14(A). It was confirmed that inside the hemispherical particles was not hollow but dense, as in FIG. 10 of Example 1.

It was confirmed from FIGS. 13 and 14 that the mechanism by which the film of the present invention is formed with the use of the method of the present invention was in agreement with the mechanism described with reference to FIG. 4 for illustrative purpose.

FIG. 15 shows SEM images of the films produced in Example 3.

FIGS. 15(A), (B), and (D) are SEM images of the films produced from the benzene solution added in different amounts (20 μL (4.1 μL/cm$^2$), 40 μL (8.2 μL/cm$^2$), and 100 μL (20.4 μL/cm$^2$)). FIG. 15(C) is the same as FIG. 6(B) (70 μL (14.3 μL/cm$^2$)) of Example 1.

From FIG. 15(A), formation of the ultrathin film 410 (FIG. 4) was confirmed. Formation of hemispherical particles by nucleus growth was confirmed in FIG. 15(B); however, the arrangement was somewhat random. Formation of hemispherical particles by nucleus growth was confirmed in FIG. 15(D); however, the particle monodispersity was poor, and the shape and arrangement were somewhat random. From these results, it was confirmed that the benzene solution should be spread over the water surface in a 14 μL±0.5 μL/cm$^2$ range (a 66 μL to 71 μL range for the effective spread area of 4.9 cm$^2$) in order to reliably obtain the film of the present invention formed by the hemispherical particles of a hexagonal close-packed structure-like organization.

FIG. 16 shows SEM images of the films produced in Comparative Example 1.

FIG. 16(A) to (C) are SEM images of the films produced from different lower aqueous phases, specifically, a mixed solution of methanol and water, a mixed solution of ethanol and water, and a mixed solution of propanol and water. FIG. 16(D) is the same as FIG. 6(B) (the lower aqueous phase is water) of Example 1.

Referring to FIG. 16(A) in which the lower aqueous phase is a mixed solution of methanol and water, formation of hemispherical particles by nucleus growth was confirmed. However, the arrangement was random. On the other hand, in FIGS. 16(B) and (C) in which the lower aqueous phase is a mixed solution of ethanol and water or a mixed solution of propanol and water, distinct hemispherical particles were not obtained, and the product film was a simple disordered aggregate with no monodispersity.

The following considers surface tension. Spreading coefficient S is represented by $S=\gamma_a-\gamma_{o/w}-\gamma_o$ (wherein $\gamma_a$ is the water/gas surface tension, $\gamma_{o/w}$ is the oil/water surface tension, and $\gamma_o$ is the oil/gas surface tension). Positive spreading coefficient S means the higher ability to spread the solvent. The surface tension of water, the surface tension of the water/methanol mixed solution, the surface tension of the water/ethanol mixed solution, and the surface tension of the water/propanol mixed solution were 72.75 mN/m, 44.28 mN/m, 36.09 mN/m, and 28.88 mN/m, respectively. Upon calculations of the spreading coefficient S for each lower aqueous phase using the surface tensions, positive spreading coefficients S were yielded for water and benzene, whereas the spreading coefficients S were negative for the mixed solutions of other alcohols and water, and benzene. This is suggestive of the benzene not easily spreading on the mixed solution of alcohol and water, and is in good agreement with the result presented in FIG. 16.

From these results, it was confirmed that water alone is preferable as the lower aqueous phase in the method of the present invention.

FIG. 17 shows SEM images of the films produced in Comparative Example 2.

FIG. 17(A) to (D) are SEM images of the films produced with toluene, m-xylene, $CHCl_3$ (chloroform), and $CH_2Cl_2$ (dichloromethane) used as the solvents of the fullerene derivative $(3,4,5)C_{20}$-$C_{60}$. Referring to FIG. 17(A) in which the solvent is toluene, formation of the hemispherical particles by nucleus growth was confirmed. However, the monodispersity was poor, and the arrangement was random. Referring to FIG. 17(B) to (D) in which m-xylene, chloroform, and dichloromethane were used as solvents, no distinct hemispherical particles were obtained.

The following considers solvent evaporation rate. The evaporation rates of benzene, toluene, m-xylene, chloroform, and dichloromethane are 5.1, 2.2, 0.6, 11.6, and 27.5, respectively, relative to the evaporation rate of butyl acetate taken as 1. By comparing these values and FIG. 17, it was found that the solvents (toluene, m-xylene) with the faster evaporation rates than that of benzene, and the solvents (chloroform, dichloromethane) that evaporate more slowly than benzene failed to grow hemispherical particles having excellent monodispersity and to produce a film having a hexagonal close-packed structure-like organization.

These results confirmed that benzene is preferable as the solvent of the fullerene derivatives of the formula (1) in the method of the present invention.

FIG. 18 shows SEM images of the films produced in Comparative Example 3.

FIG. 18(A) to (C) are SEM images of the films using $C_{60}$, $(3,4)C_{20}$-$C_{60}$, and $(3,4,5)C_{16}$-$C_{60}$ as the solutes of the spread solutions. No distinct hemispherical particles were obtained in all films, and, unlike the present invention, the film formed of hemispherical particles having a hexagonal close-packed structure-like organization was not obtained. Referring to FIG. 18(A), the $C_{60}$ had stronger interactions than the $(3,4,5)C_{20}$-$C_{60}$, suggesting that the $C_{60}$ is more likely to aggregate. On the other hand, the $(3,4)C_{20}$-$C_{60}$ and $(3,4,5)C_{16}$-$C_{60}$, despite the structures very similar to that of $(3,4,5)C_{20}$-$C_{60}$, had intermolecular forces slightly different from that of the $(3,4,5)C_{20}$-$C_{60}$. The producing method of the present invention was therefore not applicable, and improvements are needed. These results confirmed that the fullerene derivatives of the formula (1) are preferable as the solute of the spread solution in the method of the present invention.

FIG. 19 shows BAM images of the films produced in Example 4 and Comparative Example 4.

FIG. 19(A) to (F) shows BAM images of the films produced with benzene, toluene, chloroform, dichloromethane, m-xylene, and p-xylene used as solvents. As can be seen in FIG. 19(A), the film was found to be highly homogeneous. Referring to FIG. 19(D), the film was a partially aggregated film, even though it was relatively homogeneous. The films shown in FIGS. 19(B), (C), (E), and (F) were all aggregated as a whole.

FIG. 20 shows SEM images of the films produced in Example 4 and Comparative Example 4.

FIG. 20(A) to (E) shows SEM images of the films produced with benzene, toluene, chloroform, dichloromethane, and m-xylene used as solvents. As can be seen in FIG. 20(A), the hemispherical particles were observed throughout the film, and were organized like a hexagonal close-packed structure. However, by comparing FIG. 20(A) and FIG. 6, the quality of the film of FIG. 20(A) was found to be slightly inferior to the film of FIG. 6. This suggests that the benzene evaporation in step S220 (FIG. 2) of the method of the present invention should more preferably be performed under sealed conditions, even considering that the concentration and the spread amount of the benzene solution of Example 4 are set to values below those used in Example 1 (for example, below the preferred spread amount of 13.5 $\mu L/cm^2$ to 14.5 $\mu L/cm^2$) to examine the initial appearance.

As can be seen in FIG. 20(D), the film using dichloromethane as the solvent showed formation of the hemispherical particles by nucleus growth (however, the hemispherical particles contained large numbers of large air spaces). However, the arrangement was random. This result is in agreement with the result presented in FIG. 19(D).

Referring to FIG. 20(B) showing the film using toluene as the solvent, particulate material was confirmed. However, the particulate materials was not hemispherical particles. Considering the solvent evaporation rate, it is speculated that the mechanism by which the hemispherical particles are formed with the solvent toluene is relatively mild as with the case of benzene, because the evaporation rate of toluene is relatively close to that of benzene. However, because the fullerene derivatives aggregate differently when benzene and toluene are used as solvents, it is speculated that the resulting film does not contain the hemispherical particles having a hexagonal close-packed structure-like organization.

Referring to FIGS. 20(C) and (E), the films using chloroform and m-xylene as solvents both appeared aggregated. This result is in agreement with FIGS. 19(C) and (E).

Figure 21:
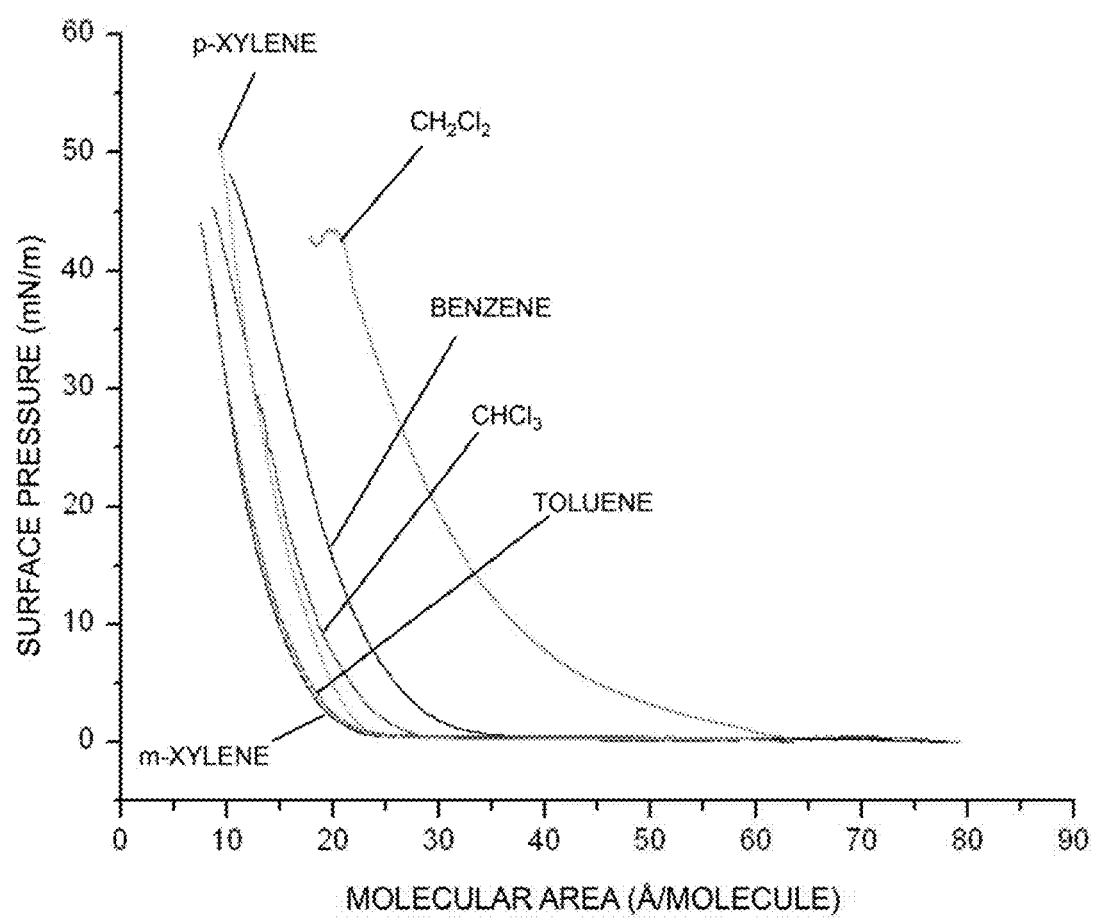
FIG. 21 is a diagram representing surface pressure-molecular area isotherms of the films produced in Example 4 and Comparative Example 4.

FIG. 21 is a diagram representing surface pressure-molecular area isotherms of the films produced in Example 4 and Comparative Example 4.

As can be seen in FIG. 21, formation of the Langmuir film was possible with any solvent of the fullerene derivative $(3,4,5)C_{20}$-$C_{60}$. Judging from the area occupied per molecule (about 1.0 $nm^2$/molecule), multilayer film formation was confirmed for all solvent systems. However, it was found that the behaviors of the films using benzene and dichloromethane required greater surface pressures compared to the behaviors of the films using p-xylene, m-xylene, and chloroform. This suggests that a film of desirable quality is more likely to result when benzene and dichloromethane are used as solvents, because the fullerene derivatives undergo grain growth (crystallization) in the dispersed state. The finding also suggests that the fullerene derivatives tend to three-dimensionally aggregate, and randomly occur when the solvent is p-xylene, m-xylene, or chloroform. These results are in good agreement with FIGS. 19 and 20.

Figure 22:
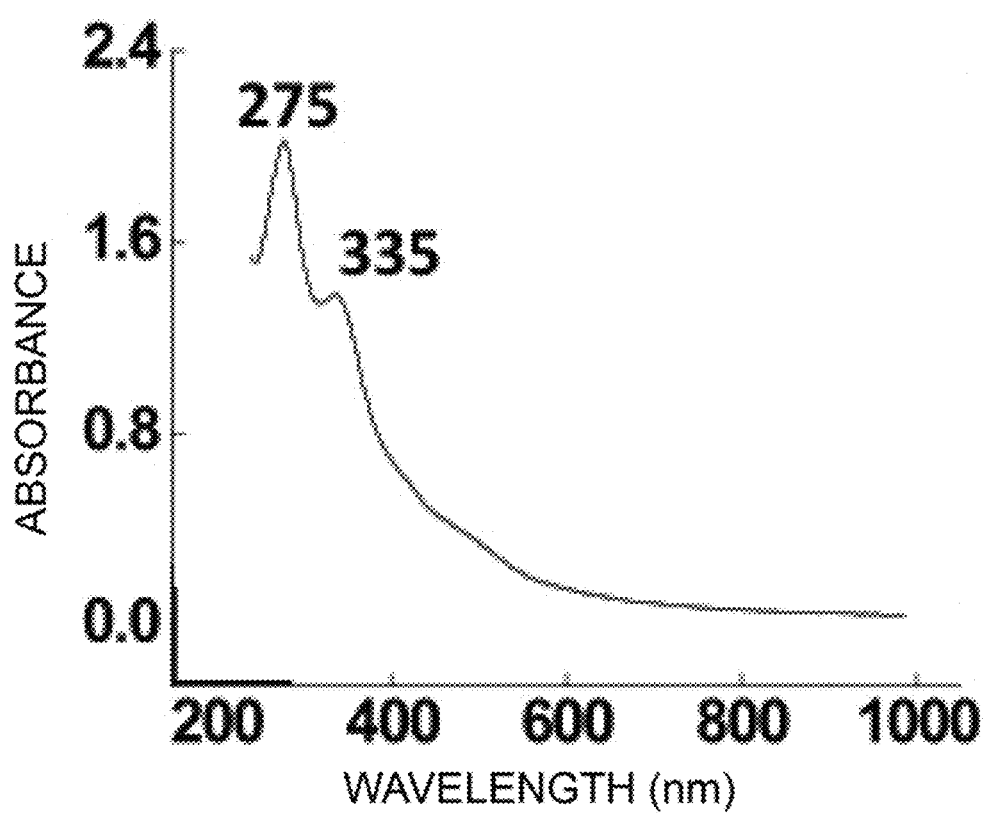
FIG. 22 is a diagram representing a UV-Vis spectrum of the film produced in Example 4.

FIG. 22 is a diagram representing a UV-Vis spectrum of the film produced in Example 4.

Figure 23:
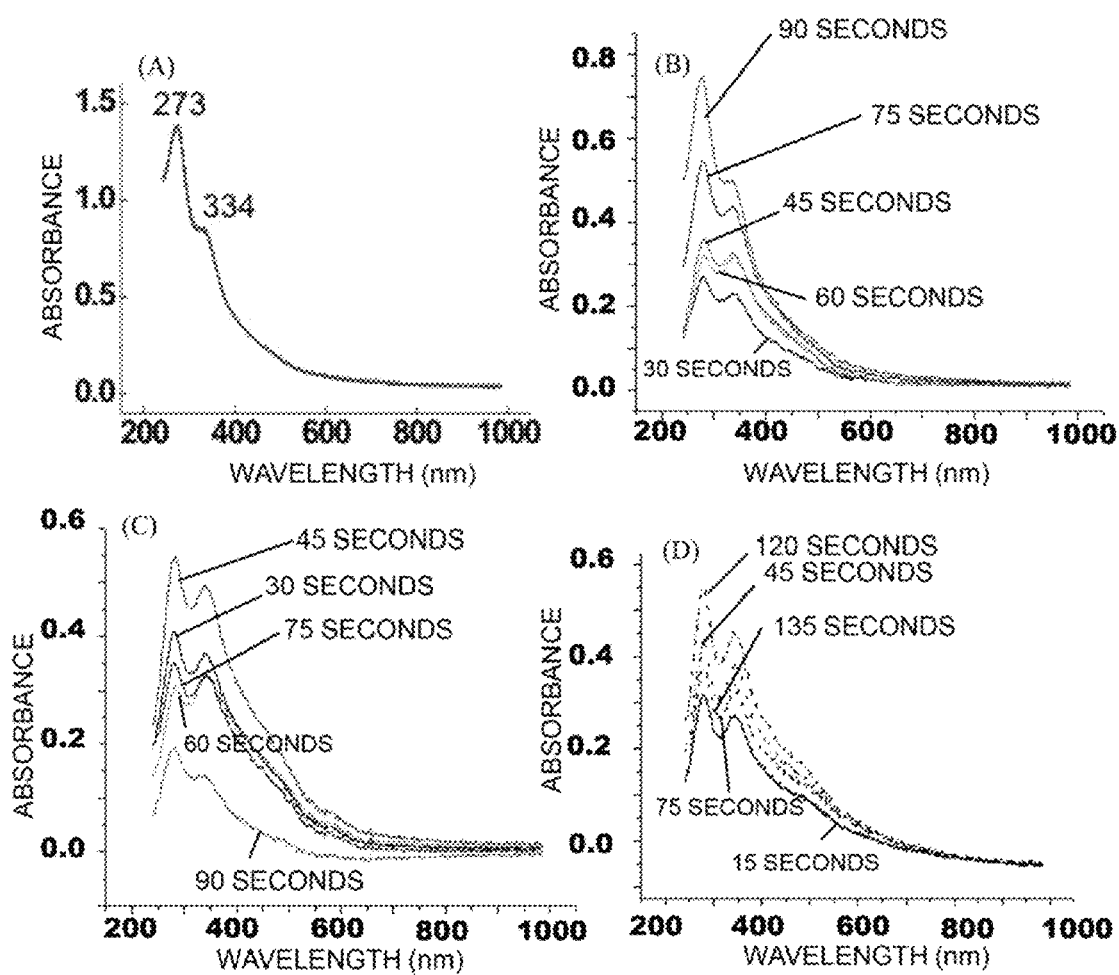
FIG. 23 shows UV-Vis spectra of the films produced in Comparative Example 4.

FIG. 23 shows UV-Vis spectra of the films produced in Comparative Example 4.

Referring to FIG. 22, the film of Example 4 had the same UV-vis reflection spectra after 30, 45, 60, 75, 90, and 105 seconds from spreading the benzene solution, and there was no time dependence. Peaks occurred at 275 nm and 335 nm wavelengths in all UV-vis reflection spectra.

FIG. 23(A) to (D) represents UV-Vis spectra of the films that use dichloromethane, toluene, chloroform, and m-xylene as solvents. Referring to FIG. 23(A), the UV-vis reflection spectra after 30, 45, 60, 75, 90, and 105 seconds from spreading the dichloromethane solution were the same, and there was no time dependence, as in FIG. 22. Peaks occurred at 273 nm and 334 nm wavelengths in these UV-vis reflection spectra. On the other hand, in FIG. 23(B) to (D), the peak intensity varied with time, even though the peaks occurred at similar wavelengths (peak wavelengths of 274 nm and 336 nm for toluene; peak wavelengths of 277 nm and 334 nm for chloroform). The time dependence of peak intensity indicates that the thin film is nonuniform at the air-liquid interface owning to the absence of surface pressure compression.

It has been shown that a solution uniformly dispersing the fullerene derivative $(3,4,5)C_{20}$-$C_{60}$ in dichloromethane (dichloromethane dispersion) has an absorption spectrum with peaks occurring at 256 nm and 317 nm. On the other hand, referring to FIG. 23(A), it was found that the film using dichloromethane as the solvent had peak wavelengths (273 nm and 334 nm) shifted toward the shorter wavelength side by 17 to 19 nm and 17 to 18 nm, respectively, from the peak wavelengths (256 nm and 317 nm) of the dichloromethane dispersion. This means that the $C_{60}$ moieties in the film are in the aggregated state because of the $\pi$-$\pi$ electronic interactions.

The result that the peak positions were not solvent-dependent in FIGS. 22 and 23 confirmed that the all films were of the same components. Further, because the peak intensity was time dependent, the presence of signal variation was speculated from the formation of the aggregated nonuniform films with toluene, chloroform, and m-xylene used as solvents. This is in good agreement with the result of FIG. 21 showing that these solvents are likely to cause three-dimensional aggregation of $(3,4,5)C_{20}$-$C_{60}$.

Figure 24:
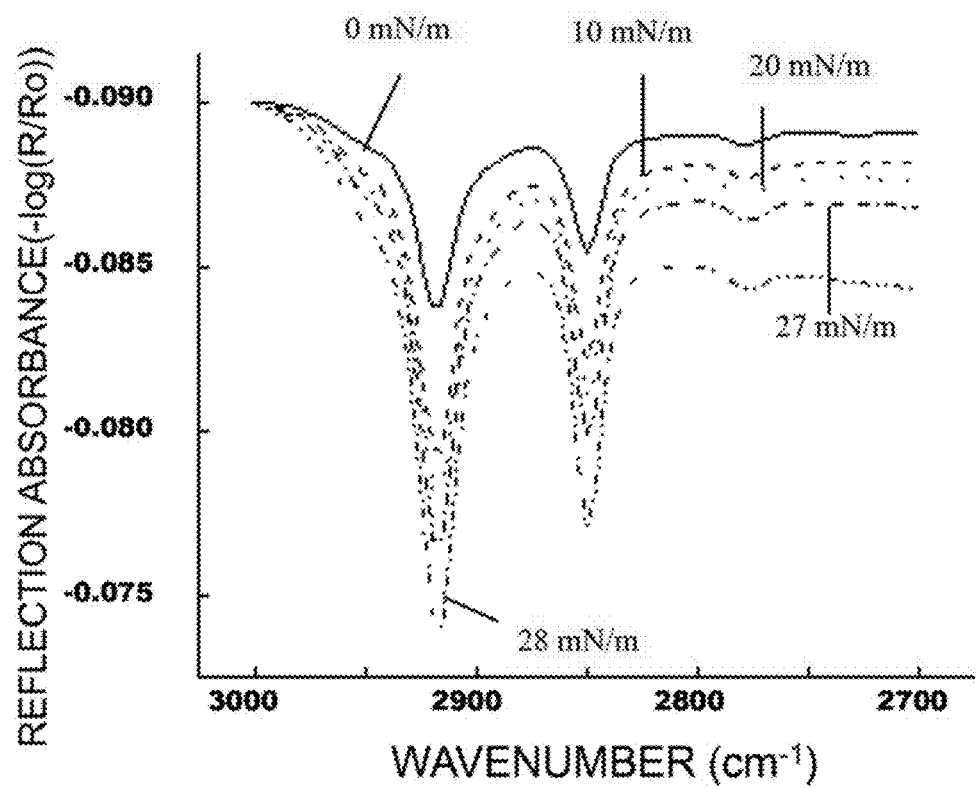
FIG. 24 shows FT-IR spectra of the films produced in Example 4.

FIG. 24 shows FT-IR spectra of the films produced in Example 4.

Figure 25:
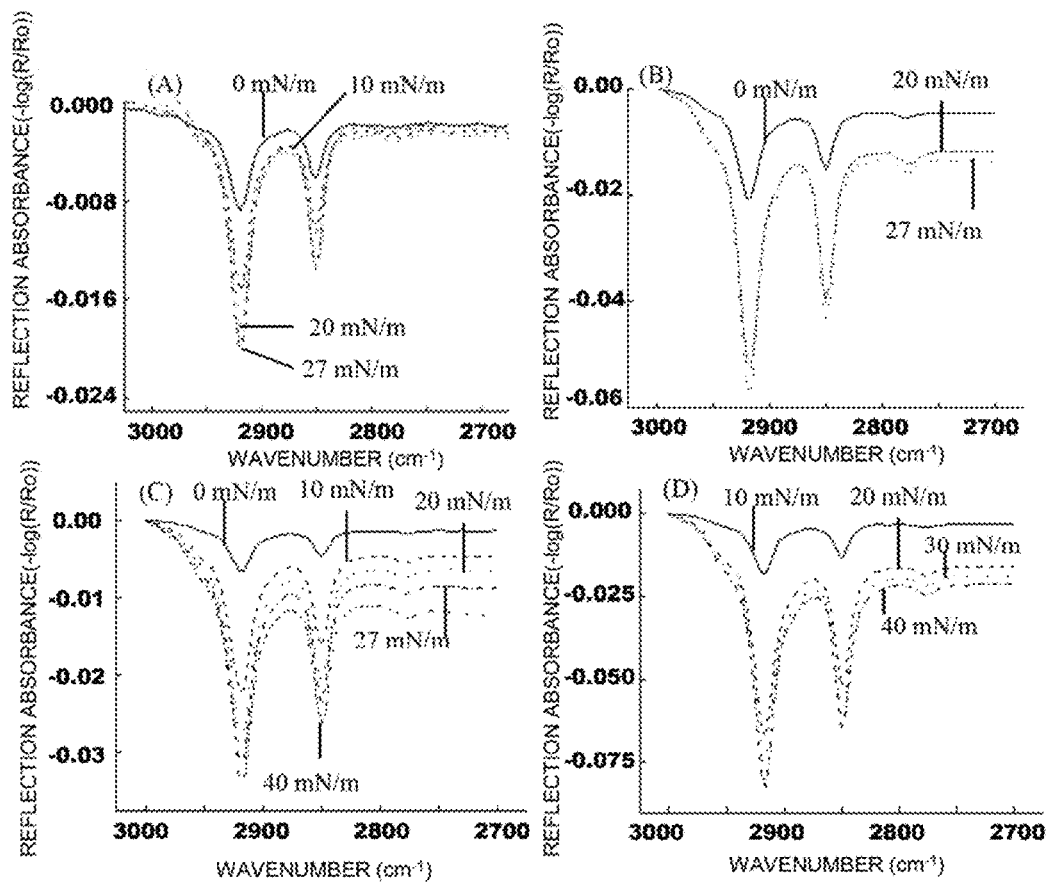
FIG. 25 shows FT-IR spectra of the films produced in Comparative Example 4.

FIG. 25 shows FT-IR spectra of the films produced in Comparative Example 4.

In the reflection absorbance ($-\log(R/R_0)$) shown in FIGS. 24 and 25, R is the reflectance of the films produced in Example 4 and Comparative Example 4, and $R_0$ is the reflectance of water used as the lower aqueous phase.

Referring to FIG. 24, the film of Example 4 had an asymmetrical stretch mode ($v_{as}(CH_2)$) of the methylene group at wavenumber 2918 cm$^{-1}$, and a symmetrical stretch mode ($v_s(CH_2)$) of the methylene group at wavenumber 2850 cm$^{-1}$. This suggests that the alkyloxy chains of the fullerene derivative $(3,4,5)C_{20}$-$C_{60}$ forming the hemispherical particles in the film are in the crystalline state with all-trans conformation. FIG. 25(A) to (D) represents FT-IR spectra of the films using dichloromethane, toluene, chloroform, and m-xylene as solvents. In FIG. 25, peaks occurred at similar wavenumbers as in FIG. 24. This result is in good agreement with FIGS. 22 and 23, confirming that the all films were of the same components.

By varying the surface pressure, it was found that the wavenumber of each mode was not dependent on surface pressure, confirming that surface pressure did not have any effect on the crystallinity of the alkyloxy chains of the fullerene derivative $(3,4,5)C_{20}$-$C_{60}$.

Industrial Applicability

The film of the present invention includes the hemispherical particles organized like a hexagonal close-packed structure and joined to one another, and is therefore very orderly and stable. The film is reminiscent of the retinal structure of the compound eyes of organisms such as insects. Thus, by using the film of the present invention as a template, a material of a novel structure can be provided upon transferring the form of the film of the present invention to material such as metal, polymer, and inorganic material. The film producing method of the present invention includes the simple steps of spreading a specific fullerene derivative -dissolving benzene solution over a water surface, and evaporating the benzene. The method is advantageous, because it does not require any special expensive devices, precision procedures or the like, and can thus provide the film of the present invention at low cost and in high quality, and can increase the film area with ease.

REFERENCE SIGNS LIST

100 Film
110 Hemispherical particle
120 Hexagonal close-packed structure
130 Fullerene derivative
140 Bilayer membrane structure
150 Spaces
160 Bottom surface center
310 Benzene solution
320 Water
410 Ultrathin film
420 Nucleus
430 Nucleus growth

CITATION LIST

Patent Literature

[Patent Literature 1] JP-A-2008-303148

The invention claimed is:

1. A film comprising hemispherical particles,
   wherein the hemispherical particles are organized like a hexagonal close-packed structure, and
   wherein the hemispherical particles are formed by fullerene derivatives represented by the following formula (1)

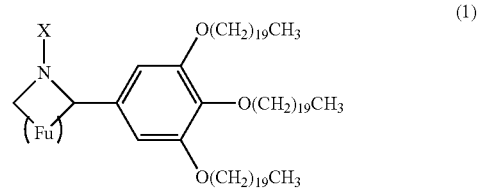

wherein X is a hydrogen atom or a methyl group and (Fu) is any fullerene.

2. The film according to claim 1, wherein the hemispherical particles have a bilayer membrane structure assembled to provide a flake-like surface for the hemispherical particles.

3. A filter that comprises the film of claim 2.

4. The filter according to claim 3, wherein the film supports semiconductor particles.

5. The film according to claim 1, wherein the hemispherical particles have a particle size ranging from 15 μm to 35 μm.

6. A filter that comprises the film of claim 5.

7. The filter according to claim 6, wherein the film supports semiconductor particles.

8. The film according to claim 1, wherein the fullerene derivatives in the hemispherical particles are distributed in a manner that makes the fullerene derivative denser at a bottom surface center and sparser toward the outer side.

9. A filter that comprises the film of claim 8.

10. The filter according to claim 9, wherein the film supports semiconductor particles.

11. A method for producing a film formed of hemispherical particles, the method comprising the steps of:
spreading over a water surface a benzene solution dissolving fullerene derivatives of the following formula (1)

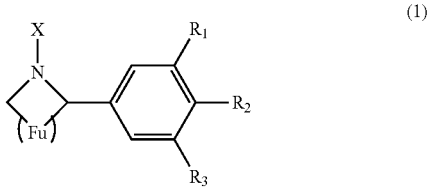

(1)

wherein X is a hydrogen atom or a methyl group and (Fu) is any fullerene; and evaporating the benzene in the benzene solution.

12. The method according to claim 11, further comprising the step of transferring the film formed of hemispherical particles obtained in the evaporation step to a substrate.

13. The method according to claim 11, wherein the benzene solution is spread in 13.5 μL to 14.5 μL per 1 $cm^2$ area of the water surface in the spreading step.

14. The method according to claim 11, wherein the benzene solution has a concentration of 1.5 mM to 2.5 mM in the spreading step.

15. The method according to claim 11, wherein the benzene solution spread over the water surface is allowed to stand at room temperature in the dark in the evaporation step.

16. The method according to claim 11, wherein the benzene solution spread over the water surface is allowed to stand under sealed conditions in the evaporation step.

17. The method according to claim 11,
wherein the film formed of hemispherical particles has a bilayer membrane structure formed by the fullerene derivatives,
wherein the bilayer membrane structure is assembled to provide a flake-like surface for the hemispherical particles, and
wherein the hemispherical particles are organized like a hexagonal close-packed structure.

18. A filter that comprises the film of claim 1.

19. The filter according to claim 18, wherein the film supports semiconductor particles.

* * * * *